(12) United States Patent
Haugen et al.

(10) Patent No.: US 7,527,592 B2
(45) Date of Patent: May 5, 2009

(54) ULTRASOUND PROBE SUB-APERTURE PROCESSING

(75) Inventors: Geir Ultveit Haugen, Oslo (NO); Kjell Kristoffersen, Oslo (NO); Douglas Glenn Wildes, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 621 days.

(21) Appl. No.: 10/719,531

(22) Filed: Nov. 21, 2003

(65) Prior Publication Data

US 2005/0113699 A1    May 26, 2005

(51) Int. Cl.
*A61B 8/00* (2006.01)
(52) U.S. Cl. ................ 600/447; 600/459
(58) Field of Classification Search ......... 600/443–447, 600/456, 458–459; 73/625–626; 367/99, 367/103–105, 119, 121–123; 128/916
See application file for complete search history.

(56) References Cited

U.S. PATENT DOCUMENTS

| | | | |
|---|---|---|---|
| 4,058,003 A | 11/1977 | Macovski | |
| 4,127,034 A | 11/1978 | Lederman et al. | |
| 4,140,022 A | 2/1979 | Maslak | |
| 4,152,678 A | 5/1979 | Shott et al. | |
| 4,170,766 A | 10/1979 | Pridham et al. | |
| 4,173,007 A | 10/1979 | McKeighen et al. | |
| 4,180,790 A | 12/1979 | Thomas | |
| 4,208,916 A | 6/1980 | Thomenius et al. | |
| 4,213,195 A | 7/1980 | Pridham | |
| 4,227,417 A | 10/1980 | Glenn | |
| 4,267,584 A | 5/1981 | McKeighen et al. | |
| 4,280,203 A | 7/1981 | Gilmour | |
| 4,288,764 A | 9/1981 | Ong | |
| 4,401,957 A | 8/1983 | Mckeighen et al. | |
| 4,458,324 A | 7/1984 | Burke et al. | |
| 4,464,726 A | 8/1984 | Chiang | |
| 4,542,653 A | 9/1985 | Liu | |
| 4,632,124 A | 12/1986 | Hiller et al. | |
| 4,787,392 A | 11/1988 | Saugeon | |
| 4,809,184 A | 2/1989 | O'Donnell et al. | |
| 5,027,820 A | 7/1991 | Pesque | |
| 5,030,953 A | 7/1991 | Chiang | |
| 5,063,541 A | 11/1991 | Kondo et al. | |
| 5,089,983 A | 2/1992 | Chiang | |
| 5,123,415 A | 6/1992 | Daigle | |
| 5,126,962 A | 6/1992 | Chiang | |
| 5,186,177 A * | 2/1993 | O'Donnell et al. | ......... 600/463 |
| 5,199,437 A | 4/1993 | Langberg | |

(Continued)

FOREIGN PATENT DOCUMENTS

DE      42 41 712 A1    6/1993

(Continued)

*Primary Examiner*—Francis J. Jaworski
(74) *Attorney, Agent, or Firm*—Pete Vogel; Dean D. Small; Small Patent Law Group

(57) ABSTRACT

A sub-aperture transceiver system for an ultrasound probe includes a signal processor, receive signal connections connecting the signal processor to a receive aperture comprising acoustic transceiver elements, and transmit signal connections coupled to a transmit aperture that includes at least one acoustic transceiver element multiplexed with the receive aperture.

32 Claims, 17 Drawing Sheets

U.S. PATENT DOCUMENTS

| | | | |
|---|---|---|---|
| 5,203,335 A | 4/1993 | Noujaim et al. | |
| 5,229,933 A | 7/1993 | Larson, III | |
| 5,249,578 A | 10/1993 | Karp et al. | |
| 5,257,629 A | 11/1993 | Kitney et al. | |
| 5,269,307 A | 12/1993 | Fife et al. | |
| 5,287,753 A | 2/1994 | Routh et al. | |
| 5,295,485 A | 3/1994 | Shinomura et al. | |
| 5,345,426 A | 9/1994 | Lipschutz | |
| 5,345,939 A | 9/1994 | Engeler et al. | |
| 5,365,929 A | 11/1994 | Peterson | |
| 5,368,037 A | 11/1994 | Eberle et al. | |
| 5,381,795 A | 1/1995 | Nordgren et al. | |
| 5,386,830 A | 2/1995 | Powers et al. | |
| 5,390,674 A | 2/1995 | Robinson et al. | |
| 5,396,285 A | 3/1995 | Hedberg et al. | |
| 5,402,793 A | 4/1995 | Gruner et al. | |
| 5,417,217 A | 5/1995 | Morita et al. | |
| 5,435,313 A | 7/1995 | Noda et al. | |
| 5,438,994 A | 8/1995 | Starosta et al. | |
| 5,450,851 A | 9/1995 | Hancock | |
| 5,456,257 A | 10/1995 | Johnson et al. | |
| 5,462,057 A | 10/1995 | Hunt et al. | |
| 5,483,963 A | 1/1996 | Butler et al. | |
| 5,522,391 A | 6/1996 | Beaudin et al. | |
| 5,528,302 A | 6/1996 | Basoglu et al. | |
| 5,573,001 A * | 11/1996 | Petrofsky et al. | 600/447 |
| 5,590,658 A | 1/1997 | Chiang et al. | |
| 5,690,114 A | 11/1997 | Chiang et al. | |
| 5,722,412 A | 3/1998 | Pflugrath et al. | |
| 5,817,024 A | 10/1998 | Ogle et al. | |
| 5,839,442 A | 11/1998 | Chiang et al. | |
| 5,957,846 A * | 9/1999 | Chiang et al. | 600/447 |
| 5,964,709 A | 10/1999 | Chiang et al. | |
| 5,997,479 A | 12/1999 | Savord et al. | |
| 6,013,032 A | 1/2000 | Savord | |
| 6,100,626 A | 8/2000 | Frey et al. | |
| 6,102,860 A | 8/2000 | Mooney | |
| 6,106,472 A | 8/2000 | Chiang et al. | |
| 6,111,816 A | 8/2000 | Chiang et al. | |
| 6,117,083 A | 9/2000 | Buck et al. | |
| 6,126,602 A | 10/2000 | Savord et al. | |
| 6,238,346 B1 | 5/2001 | Mason | |
| 6,292,433 B1 | 9/2001 | Gilbert et al. | |
| 6,375,617 B1 * | 4/2002 | Fraser | 600/443 |
| 6,440,076 B1 | 8/2002 | Sudol et al. | |
| 6,491,634 B1 | 12/2002 | Leavitt et al. | |
| 6,505,063 B2 | 1/2003 | Van Den Brink et al. | |
| 6,515,402 B2 | 2/2003 | Klee et al. | |
| 6,530,887 B1 | 3/2003 | Gilbert et al. | |
| 6,548,837 B1 | 4/2003 | Vaz De Azevedo et al. | |
| 6,552,964 B2 | 4/2003 | Chiang et al. | |
| 6,558,329 B1 | 5/2003 | Gatzke | |
| 6,582,371 B2 | 6/2003 | Miller | |
| 6,582,372 B2 | 6/2003 | Poland | |
| 6,638,226 B2 | 10/2003 | He et al. | |
| 6,671,227 B2 | 12/2003 | Gilbert et al. | |
| 6,679,849 B2 * | 1/2004 | Miller et al. | 600/463 |
| 6,721,235 B2 | 4/2004 | Chiang et al. | |
| 6,783,493 B2 | 8/2004 | Chiang et al. | |
| 6,869,401 B2 | 3/2005 | Gilbert et al. | |
| 6,969,352 B2 | 11/2005 | Chiang et al. | |
| 2002/0035328 A1 | 3/2002 | Roundhill et al. | |
| 2005/0228277 A1 * | 10/2005 | Barnes et al. | 600/437 |

FOREIGN PATENT DOCUMENTS

| | | |
|---|---|---|
| DE | 43 02 538 C1 | 4/1994 |
| EP | 0 585 070 A1 | 3/1994 |
| EP | 0 627 635 A2 | 12/1994 |
| GB | 2 219 089 | 11/1989 |
| WO | WO02/017296 A1 | 8/2001 |
| WO | WO02/017298 A1 | 8/2001 |
| WO | WO02/93548 A2 | 4/2002 |

* cited by examiner

ULTRASOUND PROBE SUB-APERTURE PROCESSING

CROSS REFERENCE TO RELATED APPLICATIONS

This application is related to Titled "Ultrasound Probe Transceiver Circuitry", filed Nov. 21, 2003, Ser. No. 10/719,431, and Titled "Ultrasound Probe Distributed Beamformer", filed Nov. 21, 2003, Ser. No. 10/719,417.

BACKGROUND OF THE INVENTION

1. Field of the Invention

This invention relates generally to ultrasound medical imaging systems. More specifically, this invention relates to processing sub-apertures of a multiple element transducer probe.

2. Related Art

Doctors and technicians commonly use medical imaging systems to obtain display, and study images for diagnostic purposes. In ultrasound imaging systems, for example, a doctor may obtain images of a patient's heart in an attempt to learn whether the heart functions properly. As time moves forward, these imaging systems become increasingly adept at obtaining not only the images but also additional related diagnostic information such as ECG traces, heart rate, and the like.

Two key components of an ultrasound system are the ultrasound probe and the beamformer. The beamformer focuses and steers ultrasound energy transmitted by and received by the probe as one step in generating images of anatomic content on a display.

Development of 3D ultrasound push towards ultrasound probes with a large number of acoustic elements. Recent technology developments suggest reducing the large number of channels by sub-grouping the aperture elements and pre-process each group into one signal that is transferred to the system. Transmit can similarly be handled by transmitters solely in the probe, or by transmitting on sub-groups of the aperture.

High quality images, of course, are of great importance in clinically evaluating the physiology that a doctor is studying. High quality images require use of a non-sparse aperture, e.g. most elements on the aperture must be used both for transmit and receive. Current system, achieve this by multiplexing between the transmit and receive circuitry in the system. Each channel in the probe can then be connected with one cable to the system and be used both for transmit and receive.

The layout and implementation of the aperture sub-grouping for transmit and receive is of great importance for the image quality. The introduction of circuitry in the probe poses technical challenges that must be solved. Also, with receive and/or transmit circuitry in the probe the current approach with a transmit/receive switch in the system does not allow use off all acoustic channels on the probe for both transmit and receive.

Therefore, there is a need to overcome the difficulties set forth above and others previously experienced.

BRIEF DESCRIPTION OF THE INVENTION

In one implementation, probe located transceiver circuitry for ultrasound transducer elements includes a transmit section and a receive section. The transmit section includes a transmit section input, a transmit section output, and receive signal blocking circuitry coupled between the transmit section input and the transmit section output. The receive section includes a receive section input, a receive section output, and transmit signal blocking circuitry coupled between the receive section input and the receive section output. The transmit section input is coupled to the receive section output. In another implementation, the transmit section input is not coupled to the receive section output.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the marking systems and methods. In the figures, like reference numerals designate corresponding parts throughout the different views.

FIG. 18 shows steps that the ultrasound probe shown in FIG. 1 may take to transmit and receive energy to an acoustic transducer element multiplexed between a receive aperture and a transmit aperture.

DETAILED DESCRIPTION

Figure 1:
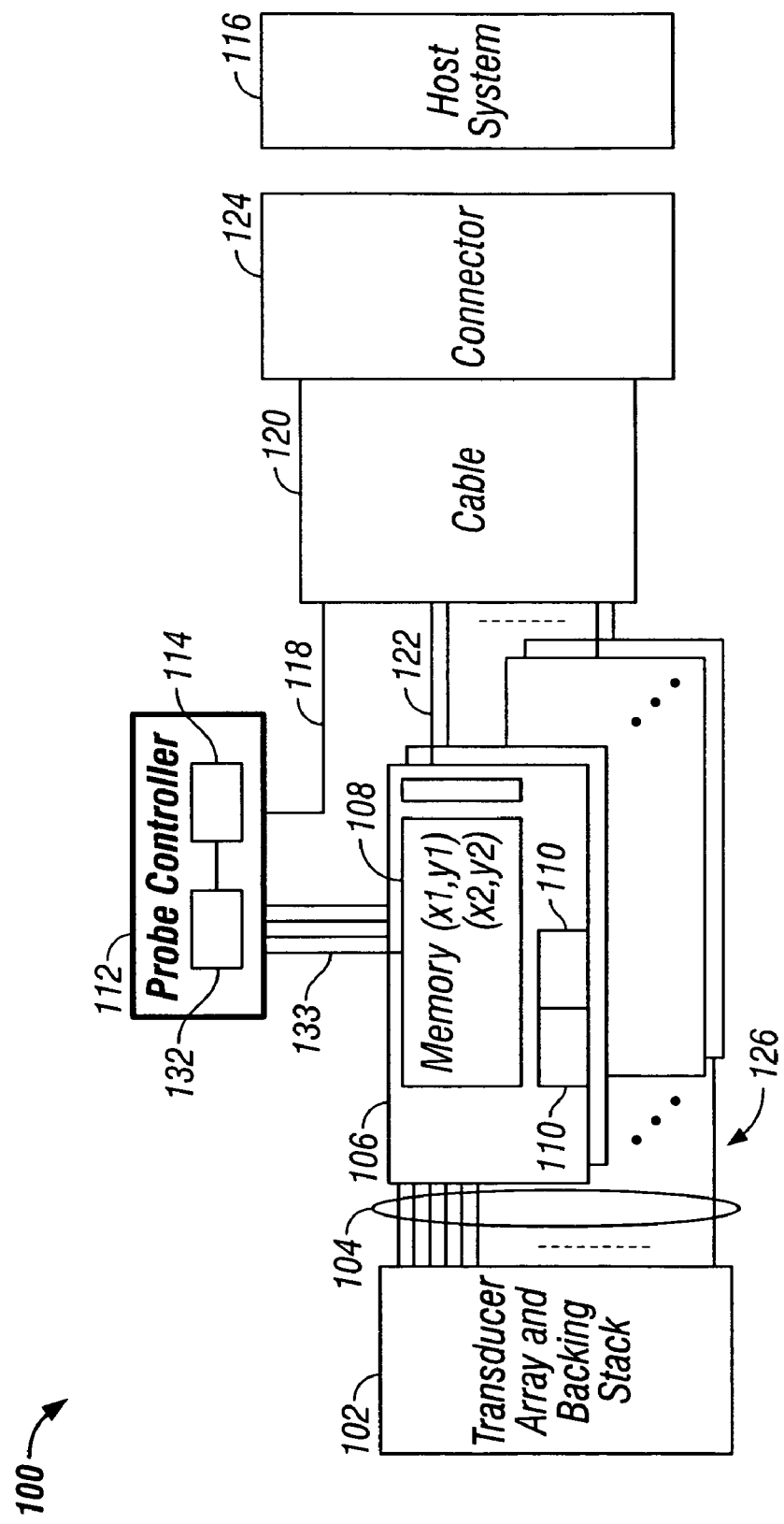
FIG. 1 illustrates a block diagram of an ultrasound probe in communication with a host system.

FIG. 1 illustrates a block diagram of an ultrasound probe 100. The probe 100 includes a transducer array and backing stack 102 (the "transducer array 102"), transducer cables 104, and multiple processing boards 106 that support processing electronics. Each processing board 106 includes a memory 108 (which may include geometry RAM, encoder RAM, location registers and control registers as noted below) and signal processors 110. A location cache memory and controller 112 (e.g., a general purpose CPU, microcontroller, PLD, or the like) is also present and includes a communication interface 114. The memory 108 may be separate or included as part of the signal processor 110.

The communication interface 114 establishes data exchange with the host system 116 over the digital signal lines 118 and through the signal cable 120. In addition, the signal cable 120 includes coaxial cables 122 that connect to the processing boards 106 to carry transmit pulse waveforms to the transducer array 102 and to carry back receive signals, after beamforming, to the host system 116. In another implementation the coaxial cables 122 only carry receive signals. The probe 100 may include the connector 124, through which the probe 100 attaches to the host system 116.

An interconnection 126 may be provided to connect the transducer flex cables 104 to the processing boards 106. The interconnection 126 thereby establish electrical connectivity between the transducer flex cables 104 and the processing boards 106. The interconnection 126 may be a connector, although other implementations are also suitable.

The transducer array 102 is bonded onto the backing stack, as will be described in more detail below with regard to FIG. 2. The transducer flex cables 104 provide electrical signal connections through the backing stack. In one embodiment, there are forty-eight (48) transducer flex cables 104, each with fifty-five (55) signal connections. Thus, the transducer flex cables 104 support transmit and receive signal connections for as many as 2640 transducer elements in the transducer array 102, although fewer are used in the implementation described below.

The interconnection 126 connects the transducer flex cables 104 to the processing boards 106. In one implementation, each processing board 106 couples to six planes of transducer flex cables 104, and thereby includes signal connections for 330 transducer elements.

The processing boards 106 may, like the flex cables 104, be formed from flex material. The processing boards 106 hold the processing electronics for the transducer array 102, including the signal processors 110 that perform beamforming on the receive apertures in the transducer array 102. The processing boards 106 also hold the transceiver circuitry for multiplexing selected acoustic transducer elements between reception and transmission, while protecting the signal processors 110 connected to the acoustic transducer elements.

As will be described in more detail below, each signal processor 110 may handle plural receive sub-apertures, for example four, defined at selected spatial locations on the transducer array 102. The receive sub-apertures may be triangular sub-apertures that include fifteen (15) acoustic transducer elements arranged, for example, as a row of five elements above a row of four elements above a row of three elements above a row of two elements above a row of one element. Furthermore, each processing board 106 may include six (6) signal processors. Thus, in the receive direction, each processing board 106 may process up to twenty (24) receive sub-apertures, each including fifteen acoustic transducer elements.

For every ultrasound beam, the cache memory and controller 112 connects over digital signal lines 133 (e.g., carried by a separate flex cable) to each signal processor controller which may be included within memory 108 on each processing board 106. The signal processor controller which may be included within memory 108 are drawn as a separate block labeled 'memory' on the processing board 106, but may also be included as part of the signal processor 110. The cache memory and controller 112 transfers static and dynamic probe setup information to the signal processor 110. Static setup information is typically spatial element locations, power settings, and delay setting mapping tables. Dynamic information is typically directional information for the sub-apertures that vary from beam to beam. The digital signal lines may include, for example, a clock line for each processing board 106, a serial command data line for each processing board 106, one or more data lines connected to each processing board 106, an output enable for one or more of the signal processors 110, and a test signal.

The cache memory and controller 112 communicates with the host system 116 over the digital signal lines 118 that may form part of a synchronous serial port, for example. To that end, the communication interface 114 and digital signal lines 118 may implement a low voltage differential signal interface, LVDS, according to the TIA/EIA-644 and IEEE 1592 standard, for example, including a coaxial cable with a grounded shield and center signal wire. The cache memory and controller 112 includes a block of cache memory 132, for example, 1-64 MBytes of static random access memory (SRAM).

The main purpose of the cache memory 132 in the cache memory and controller 112 is to keep beam dependent setup information for the sub-apertures. In one implementation this may be directional setup information for the sub-apertures. This is typically divided into pages where each page contains the signal processor 110 setup information required in relation to each shot. By loading up the cache pages with information for all shots in a scan sequence, this information is available in the probe during scanning. During scanning the probe setup information in relation to each shot can then be made available to the signal processors by transferring the relevant cache memory pointer to the cache memory and controller 112.

In one implementation, the cache memory in the cache memory and controller 132 is organized into of 512 k words× 16 bit (8 Mbit) and divided into pages of 128 words. The cache memory pointer can be set to the start of each page. The cache memory pointer may be, for example, a 12 bit pointer that may address a total of 4096 pages. When the cache memory 132 is a 4 Mbit cache, the cache memory pointer may be an 11 bit pointer to index 2048 pages. The words of a cache page are employed when writing or reading data to or from a chain of signal processors 110. The digital data lines for the signal processors 110 on each processing board may be chained through shift registers over a series of plural signal processors 110. Thus, data transferred to the signal processors 110 propagates serially through the signal processors 110. The bit from the word with the lowest address in a page will end in the LSB bit of the shift register to the last signal processor 110 in a chain when loading data. Further, the cache memory 132 is shown within the cache memory and controller 112, but in alternate implementations the cache memory 132 may be separate from the cache memory and controller 112. The cache memory may also be part of the signal processors 110.

The probe 100 response to e.g. sixteen bit commands from the host system 116. One exemplary set of commands is shown below in Table 1. Four bits in the command may be used to define the command, while twelve bits may be used as parameters for the command.

TABLE 1

| Name | Parameters Bit: 11-0 | Description | Details |
|---|---|---|---|
| WR_CTRL_REG | control registry setting | Write to control/status register | cache memory and controller register |
| WR_CACHE_PTR | 11/12 bit pointer | Set cache page pointer | The cache pointer indicates the start of the next page which will be loaded from cache memory and into the signal processors 110. |
| WR_CACHE | | Write a page from the host system 116 to the cache memory 132. | The address pointer might be automatically incremented For each word written. |
| LD_SCAN_PAR | | Write scan parameter page to signal processor 110 chain. | Updated for each ultrasound shot. |
| LD_CONFIG | | Load memories or registers in the signal processors 110. | Static configuration data. |
| DELAY_TUNE | None | Start delay calibration | Each signal processor 110 has an internal circuit to calibrate the delays. |
| SAP_RESET | What to reset | | |
| RD_CTRL_REG | Control register value returned | Read from control/status register | This register is internal to the cache memory and controller 112. |
| RD_CACHE_PTR | Pointer value returned | Read cache page pointer register | Useful for test and verification. |
| RD_CACHE | None | Read a page from cache memory 132. | The address pointer might be automatically incremented for each page read. |
| RD_CONFIG | | Read setup from signal processor 110. | E.g. through loop back from last signal processor 110 in chain. |
| CMD_ENABLE | ID code | To enable and disable command execution. | |

The purpose of the command set it to control the probe. The commands may control the cache memory and controller 112 and/or the signal processors 110. It is also desirable to include a protect mechanism to avoid undesired command execution due to noise, e.g. from the transmit pulses.

The Write Cache Pointer (WR_CACHE_PTR) command writes to the memory cache pointer register. In one implementation the parameter is a 12 bit cache pointer. The specified cache pointer is employed in the parameter field of the command when reading/writing the cache memory 132. During read/write of cache words the cache pointer might be automatically incremented. After transfer of a full page, the pointer will thus point to the start of next page. If more than 8 MBit are used, transfer of a longer cache pointer than 12 bit can be implemented as two commands.

The Write to Cache (WR_CACHE) command loads data into the cache memory 132. Data will be written to the cache page pointed to by the cache pointer. The cache pointer is automatically incremented after each word written to the cache. The location memory controller 112 may send a command echo when this command is received.

The Load Scan Parameters (LD_SCAN_PAR) command writes scan parameters to the signal processor 110 chain. The parameter, in one implementation, is not used. This command writes a scan parameter page to signal processors 110 from the cache page given by the cache address pointer. This command may be triggered by the EOL signal, but may also be sent as a command.

When the data is transferred, the cache memory and controller 112 sends a calculate command to the signal processors 110 to initiate calculation of beamforming delays for the next ultrasound shot (using previous loaded setup values to save setup time). The cache memory 132 pointer is automatically incremented after each word that is written to the signal processors 110. The size of a scan parameter page may be, for example, 128 words. The word with the lowest address will end up in the LSB bit in the shift register in the last signal processor 110 in a chain.

The Load Configuration (LD_CONFIG) command loads the static setup information to the signal processor 110. Static setup information is typically spatial element locations, power settings, and delay setting mapping tables inside a signal processor 110. Each time the command is used one cache page is written to the selected memory. Some loads may require more than one cache page.

Within the signal processor the Geometry RAM holding the spatial element location may be implemented as 64 words, each 12 bits in length. The Encoder RAM holding the delay-mapping table may be implemented as 1024 words, each 5 bits in length. The start address is taken from cache memory 132 address pointer. After each page, the address pointer is incremented to next cache page. Subsequent pages may thus be loaded without updating the address pointer. The word with the lowest address in a page is the first data clocked into the signal processor 110 chain. Thus, the content of the lowest address will end up in the LSB bit of the shift register of the last signal processor 110 in the chain of signal processors 110 on a particular processing board 106.

The Initiate Delay Tuning (DELAY_TUNE) command initiates the process of calibrating the internal delays in the signal processors 110. The parameter need not be used. The result is written to the analog multi-purpose register present in the signal processor 110.

The SAP Reset Command (SAP_R_SET) command resets all the internal functions or address counters in a signal processor 110. The parameter may specify a bit pattern that selects between resetting the entire signal processor 110 or sub functionality only.

The Read Control Register (RD_CONTROL_REG) command reads the control register inside the location memory controller 112. The register content may be returned in the parameter field of the command.

The Read Cache Pointer (RD_CACHE_PTR) command reads the cache memory 132 pointer register. The value read from the cache pointer register may be returned in the parameter field of the command before the command is echoed back to the host system 116.

The Read Cache (RD_CACHE) command reads data from the cache memory 132 to the host system 116. Once the command is received the location memory controller 112 may send data words as a continuous sequence of words.

The Read Configuration from SAP (RD_CONFIG) command reads configuration data from the signal processors 110 specified by the parameter bits Configuration data is read from the signal processors 110 and placed in the cache memory 132 in the cache page pointed to by the cache pointer. The cache address is incremented for each word read. The first word is placed in the lowest cache address. The cache address is adjusted to the start of next page when finished.

The Command Enable (CMD_ENABLE) command enables or disables command execution. After loading of scan parameters from the cache memory 132 command execution is disabled after the command is finished. Nevertheless, while disabled, the location memory controller 112 may still respond to the command enable command and the read control register command. A unique bit pattern may be added to the parameter field to reduce the possibility for this command to be generated from noise present on the command line.

As an overview, the following steps occur during scanning. First, an EOL signal (end of receiving data from previous ultrasound shot) triggers the cache memory and controller 112 to send a calculation command to signal processors 110, then transfer of a new page from the memory cache 132 to the signal processors 110. A page pointer register in the cache memory and controller 112 holds the start address for this new page. Prior to each upload the system host 116 sends the page pointer for the next ultrasound shot down the digital signal lines 118 to the cache memory and controller 112. When the page load is finished, an acknowledge signal might be sent back to the system host 116. The system host 116 then fires the ultrasound shot and acquisition of ultrasound data continues. When acquisition of the current shot is finished, the location memory controller 112 receives a new EOL and the process starts over again.

When the probe 100 is connected to the host system 116, the host system 116 transfers the setup information for each aperture and each beam into the SRAM on the location memory controller 112. The receive beamforming is split between the host system 116 and the probe 104. The host system 116 is responsible for the beamforming delay, aperture expansion, and amplitude apodization of the system receive channels driven by the signal processors 110 on the receive aperture outputs.

The signal processors 110 perform the beamforming on the individual receive sub-apertures. In one implementation, groups of fifteen transducer elements, arranged as triangular receive sub-apertures, are coupled to the signal processors 110. The signal processors 110 apply a delay to each of the receive signals arising from each of the transducer elements. The signal processors 110 also add the fifteen receive signals together and drive the aperture sum back to the host system 116 over the receive aperture outputs and the coaxial cables 122.

In one implementation using phase delays, each signal processor 110 includes, for each receive sub-aperture, fifteen (15) low noise amplifiers, fifteen (15) phase inverters, a capacitor switching network, and a two phase shifter that applies a 90 degree differential phase shift. In this embodiment the differential phase shift is wideband. The switching network applies weighting factors to the potentially inverted receive signals for summation into the phase shifters. In another implementation the signal processor are based on a delay line chain.

During operation, each signal processor 110 is configured so that the beamsteering for each receive sub-aperture points toward a focal point selected by the host system 116. To this end, the signal processor 110 determines the beamforming phase shifts based on the transducer element position within the receive aperture, the steering direction, and the receive frequency. Note that each receive sub-aperture need not use the same focal point and that receive sub-apertures farther away from the center of the transducer array 102 may be turned on later to achieve dynamically increasing aperture sizes.

The configuration of the signal processor 110 occurs in two steps. First, during probe 100 initialization, the host system 116 loads static signal processor setup information via the cache memory and controller 112 into the signal processor 110. This static information includes the geometry information, i.e., the spatial (x,y) location of the transducer elements in each receive sub-aperture and a frequency dependent translation table. Second, prior to scanning the dynamic setup information is transferred to the cache memory 132 in the cache memory and controller 112. Each one of these cache pages contains steering parameters for all sub-apertures in the probe in relation to one shot. In another implementation more than one cache page could be used to transfer the required beam related setup information.

During scanning, the host system 116 provides a beam index to the cache memory and controller 112. In response, the cache memory and controller 112 transfers the appropriate steering parameters from its cache memory to the signal processors 110. The signal processors 110 then determine beamforming delays based on the transducer element positions, the steering direction (as represented by the direction parameters). For the implementation using phase delays, the delays are converted to phase settings using the frequency dependent translation table.

Figure 2:
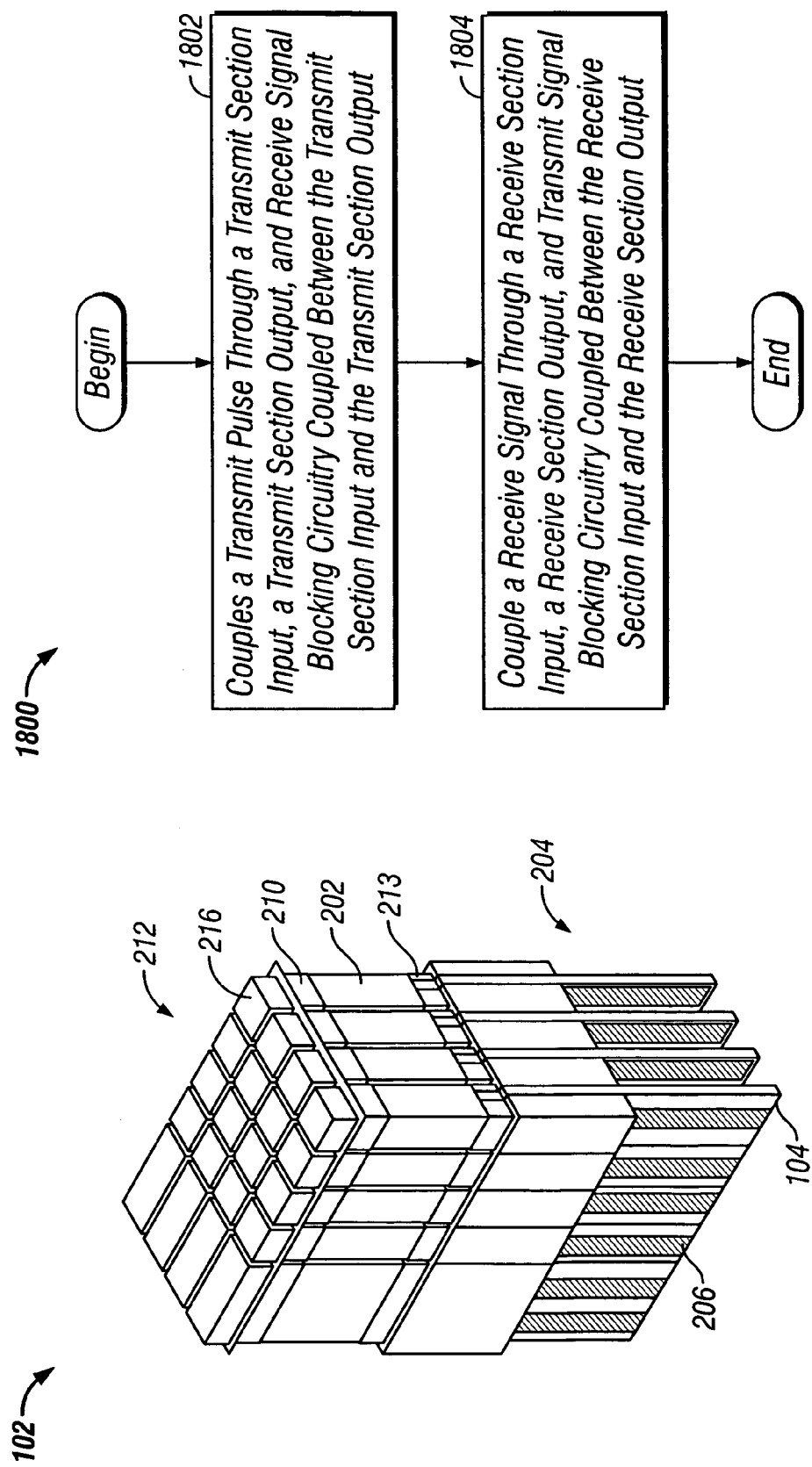
FIG. 2 shows a transducer stack including an array of acoustic transducer elements that may be used in the ultrasound probe shown in FIG. 1.

Turning next to FIG. 2, that figure shows one implementation of the transducer array 102. The transducer array 102 includes piezoelectric ceramic 202 that converts electrical-to-acoustic and acoustic-to-electrical energy. The piezoelectric ceramic 202 is located within the center of the transducer array 102. On the signal side, the piezoelectric ceramic 202 is attached to a z-axis backing layer 204 with transducer flex cables 104.

The transducer flex cables 104 provide for high density signal connection. The ceramic 202, an electrically conductive inner acoustic matching layer 210, and the top surface of the backing block 204 form discrete acoustic elements 212 centered over each of the flex circuit traces 206 in the transducer flex cables 104. Thus, there is a signal plane 213 on the z-axis backing block 204.

Each circuit trace 206 contacts the bottom, or signal side, of one transducer element 212. This diced matching layer 216 is attached to the top of each element 212 to form a ground connection across the transducer array 102 face.

Figure 3:
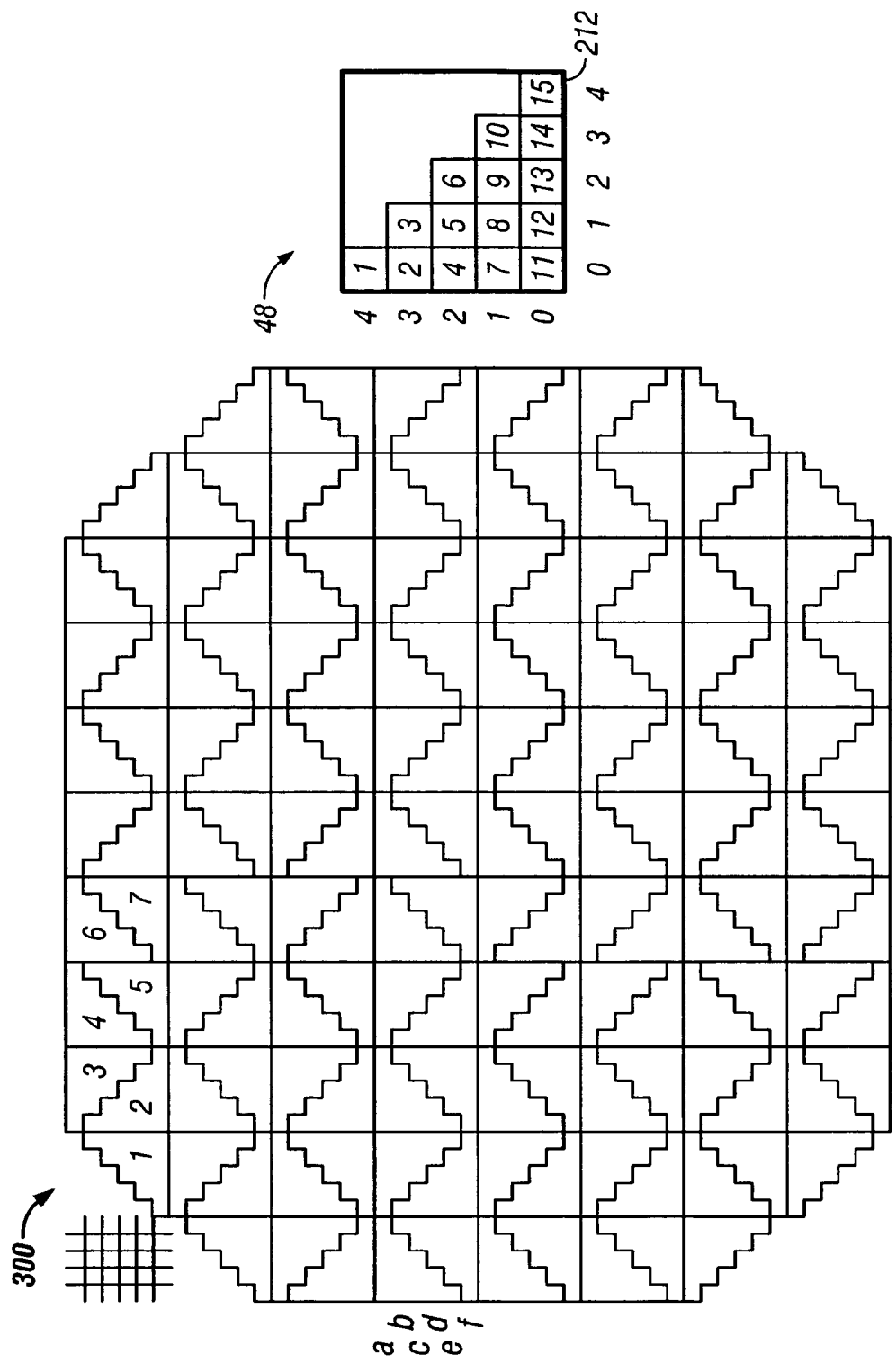
FIG. 3 shows receive apertures arranged across an array of acoustic transducer elements incorporated into the ultrasound probe shown in FIG. 1.
Figure 4:
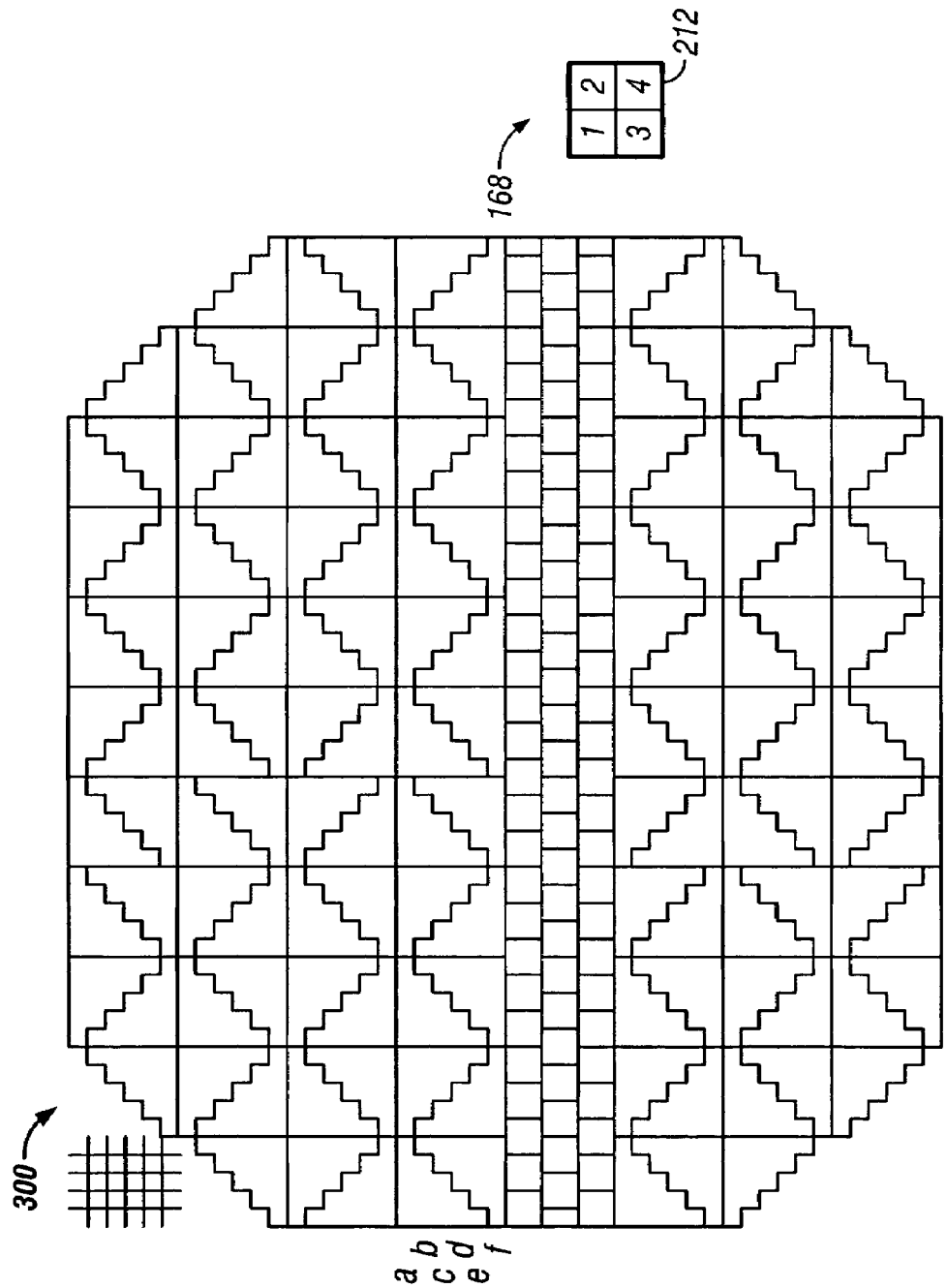
FIG. 4 depicts the transmit apertures multiplexed with receive apertures arranged across an array of acoustic transducer elements incorporated into the ultrasound probe shown in FIG. 1.

With regard next to FIGS. 3 and 4, FIG. 3 shows receive sub-apertures arranged across an array of acoustic transducer elements 300 incorporated into the ultrasound probe shown in FIG. 1. Similarly, FIG. 4 shows the transmit sub-apertures for one row, multiplexed with certain receive apertures arranged across the array of acoustic transducer elements 300. The other rows shown also contain transmit elements. In one embodiment, the array includes 55 transducer elements in the lateral direction and 48 elements in the elevational direction.

However, in the implementation described below, the corners of the array are omitted which gives the array 300 an octagonal shape. All of the transducer elements, grouped into fifteen element receive sub-apertures, are used in the receive direction as shown in FIG. 3. All transmit elements, grouped into four element transmit sub-apertures are also used in the transmit direction as shown in FIG. 4.

With reference specifically to FIG. 3, each signal processor 110 combines the fifteen receive signals arising from the fifteen transducer elements for each receive sub-aperture into a single system receive channel. The signal processor 110, as noted above, applies a delay to each receive signal before summing the receive signals. The groups of 15 transducer elements form triangular apertures as indicated in FIG. 3. Thus, the overall transducer receive aperture includes 160 sub-apertures including 160*15=2400 transducer elements. In other embodiments, the numbers of receive sub-apertures and the numbers of transmit sub-apertures chosen depend on the number of system channels available for transmit and receive, the desired aperture size and shape and the transducer elements size.

As shown in FIG. 3, with respect to the enlarged receive aperture 48, each receive aperture is formed on a 5 by 5 grid of transducer elements. The receive aperture includes a first row of five transducer elements (labeled 11-15), a second row of four transducer elements (labeled 7-10), a third row of three transducer elements (labeled 4-6), a fourth row of two transducer elements (labeled 2-3), and a fifth row of one transducer element (labeled 1). Each transducer element has a location xn, yn within its sub-aperture. For example, transducer element 14 is located at xn=3, yn=0. The receive apertures are interlocked such that the combination of two receive apertures forms a rectangular patch of 5 transducer elements in lateral and 6 transducer elements in elevational direction.

With respect to FIG. 4, the shown part of the transmit aperture includes 324 transducer elements along the fifth (5) row of receive elements of the array 300. The transmit elements are grouped into 2×2 element transmit sub-apertures and each one of the transmit sub-apertures is connected to one of the system transmit channels that are carried back to the host system 116 on the coaxial cables 122. FIG. 4 shows the transmit sub-aperture 168 enlarged, including a first row of two transducer elements (labeled 3-4) and a second row of two transducer elements (labeled 1-2). The staggering of the transmit sub-apertures in the lateral (horizontal) direction is done to reduce transmit grating lobes.

In the elevation direction, three of the 2×2 transmit sub-apertures are aligned with six receive transducer elements. In the elevation (vertical direction) the overall array 300 is divided into eight groups of six rows of transducer elements each. The arrangement of the transmit and receive sub-apertures sets up the electronics partitioning. More specifically, each group of six element rows (e.g. the one labeled a-f in FIGS. 3 and 4) is connected to one processing board 106 by six transducer flex cables 104. Because no receive sub-aperture or transmit sub-aperture crosses over the partition boundary (onto two or more processing boards), the processing electronics associated with every transducer element in the six rows are entirely contained within a single processing board 106. One significant advantage is that there is no need to route analog signals from one processing board 106 to another.

Figure 5:
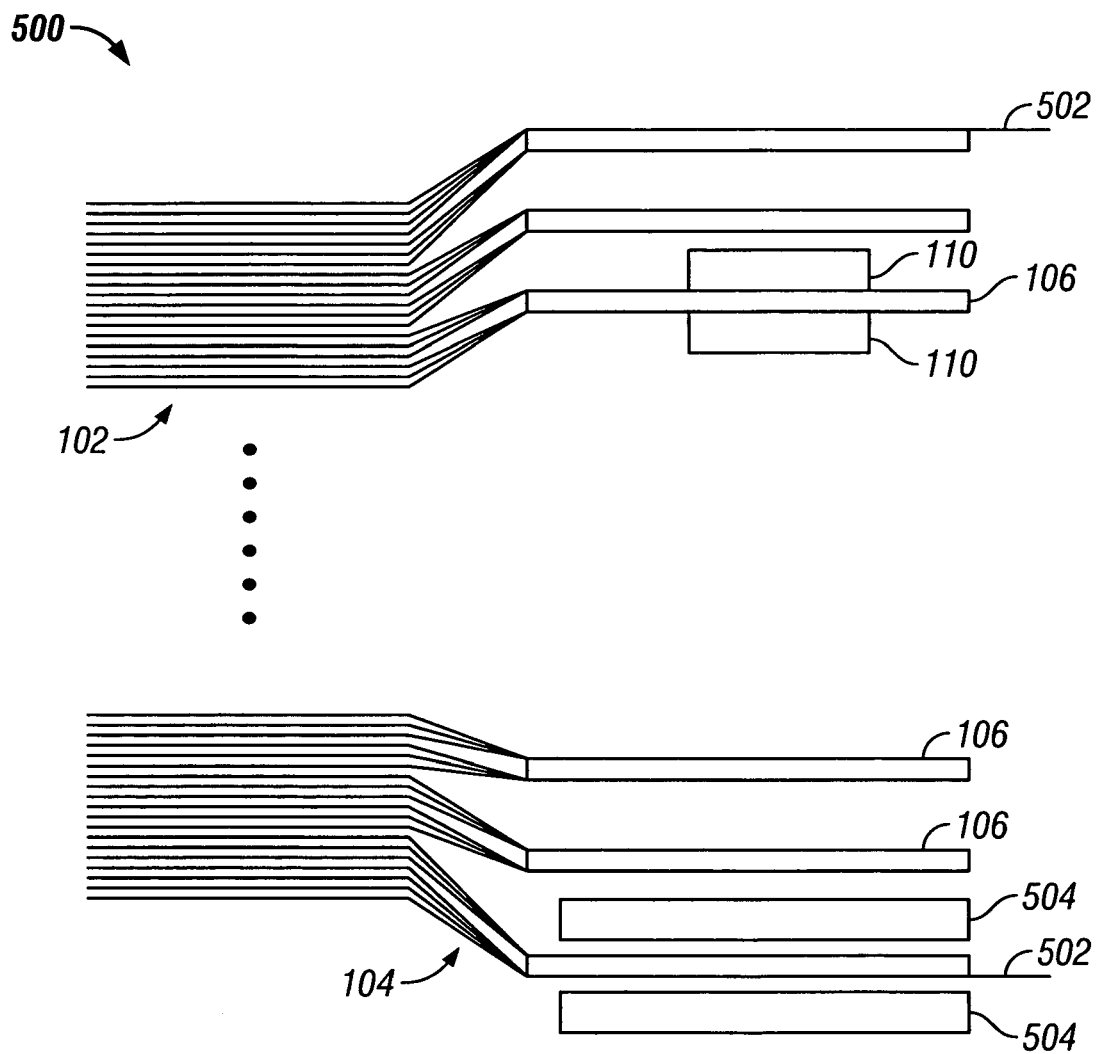
FIG. 5 shows a distribution of forty-eight (48) transducer flex cables connected to eight (8) processing boards for connecting the array of acoustic transducer elements in the probe to signal processor on the processing boards.

FIG. 5 illustrates a distribution 500 of fourty-eight (48) transducer flex cables 104 emerging from the backing stack 204 of the transducer array 102. Six transducer flex cables 104 connected to each of eight (8) processing boards 106. The transducer flex cables 104 thereby connect the array 300 of acoustic transducer elements to the signal processors (two of which are illustrated as elements 110) on the processing boards 106. Spacers 504 may be placed in between the processing boards 106 to give desired spacing.

Each transducer flex has a connection that provide signal paths for fifty-five (55) transducer elements to connect to a particular processing board. To that end a connector is provided to couple the signals from the transducer flexes 104 to the processing board 106. There are eight such processing boards 106 in the implementation described in this document. Thus, eight processing board 106, as indicated in FIG. 5, are stacked to create a complete distribution of forty-eight transducer flex cables 104 to the processing boards 106.

Figure 6:
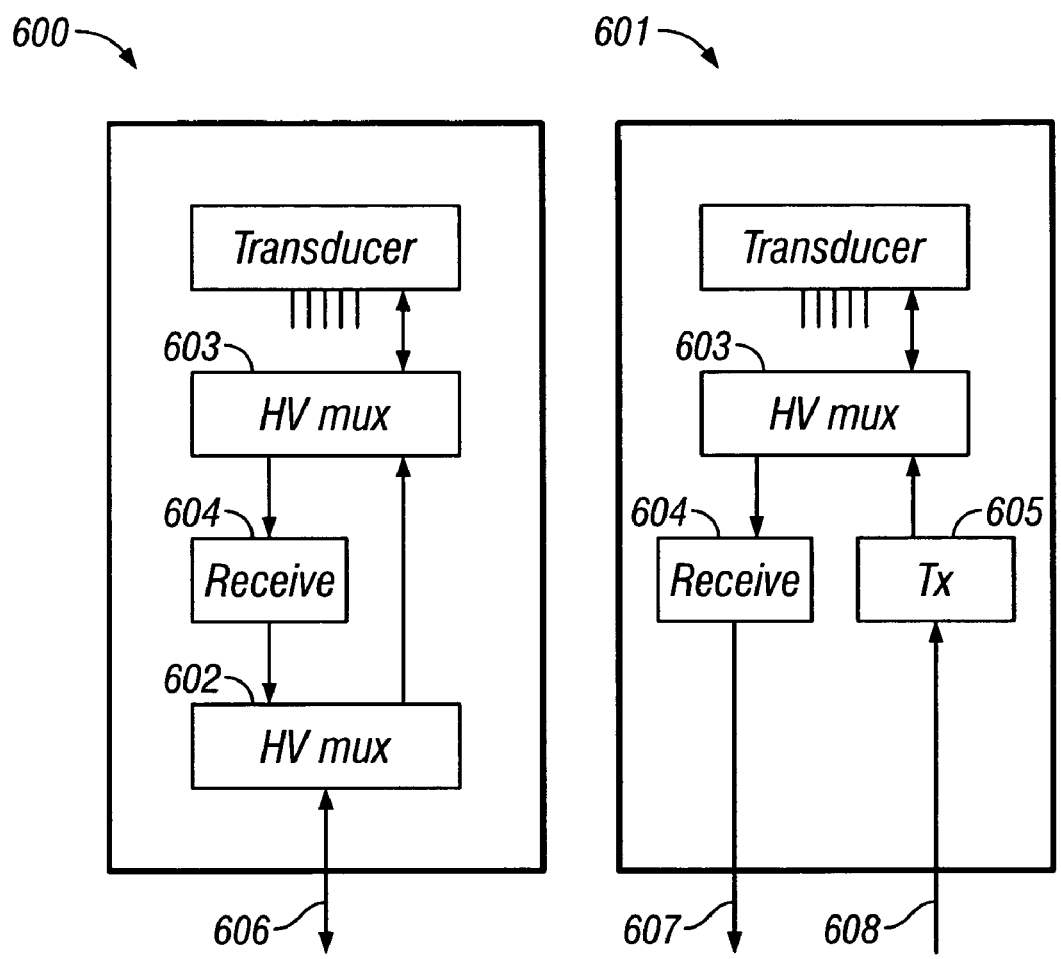
FIG. 6 illustrates transceiver circuitry for multiplexing selected acoustic transducer elements between reception and transmission, while protecting the signal processors connected to the acoustic transducer elements.

FIG. 6 shows a probe circuitry for multiplexing selected acoustic transducer elements between reception and transmission, while protecting the probe electronics for transmit and receive. The implementation 600 uses the coaxes 606 to the system for both transmit and receive. In this implementation the probe receive processing circuitry 604 must have protecting circuitry both on input 603-604 connection, and on its output 602-604 connection. In another implementation with transmit circuitry in the probe 601, only the receive circuitry input, the 603-604 connection, must be protected. In this implementation the transmit circuitry need are controlled from the system over the lines 608, or from the probe cache memory and controller 112.

Figure 7:
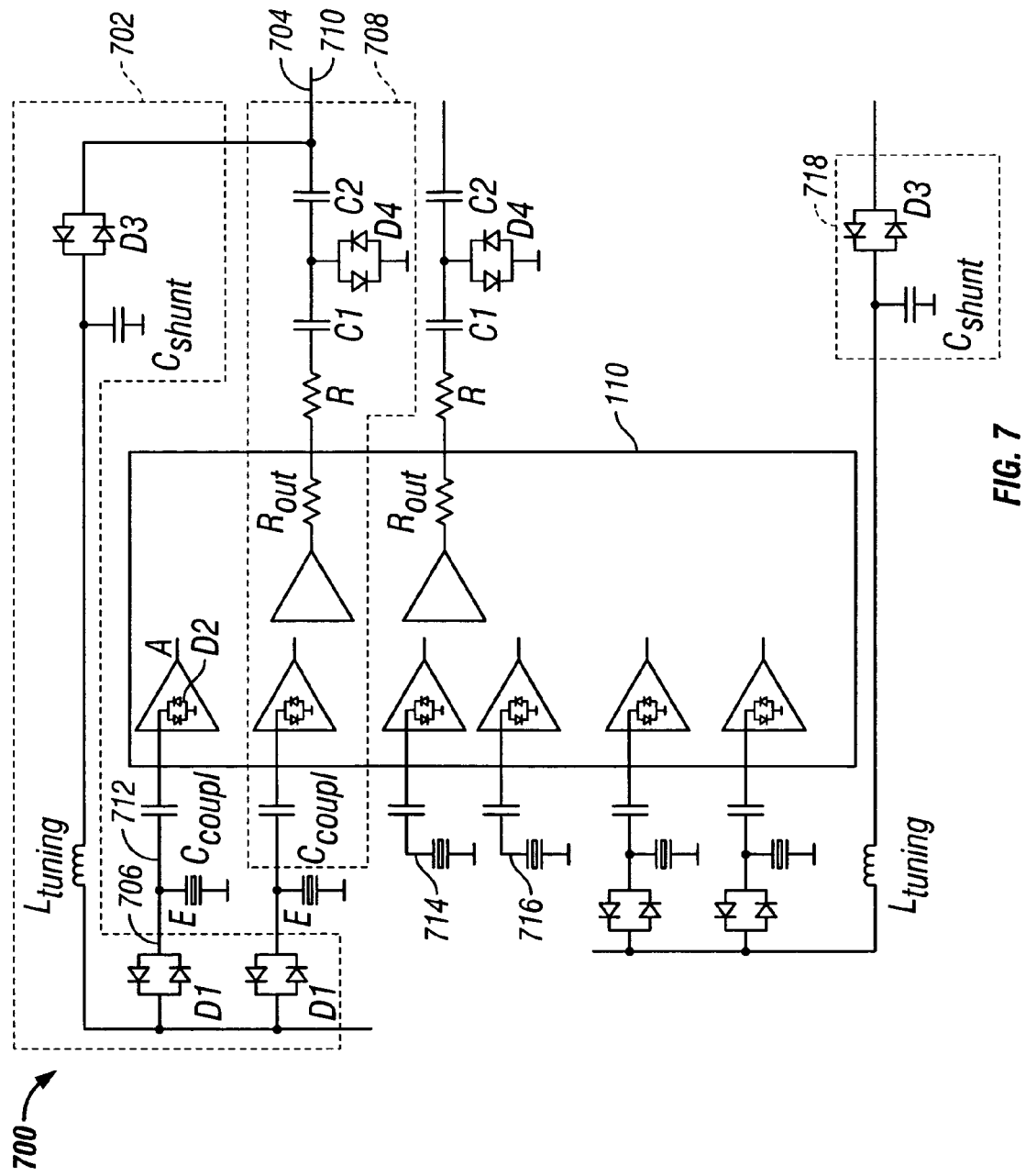
FIG. 7 illustrates one embodiment of transceiver circuitry using passive circuitry for multiplexing selected acoustic transducer elements between reception and transmission, while protecting the signal processors connected to the acoustic transducer elements.

The multiplexing circuitry 602 and 603 may be implemented using switches or passive circuitry. An embodiment with active switches, the control circuitry must be timed relative to the signal flow. An embodiment using passive circuitry, as shown in FIG. 7, is protecting the probe circuitry based on the signal levels only. For all embodiments the multiplexers or switches used must withstand the high voltage transmit voltage, typically in the range from 10 to 400 volt peak-to-peak for piezoelectric transducer elements. For other types of transducer elements, other voltage ranges may be used.

FIG. 7 shows a passive implementation of a transceiver circuitry 700 for multiplexing selected acoustic transducer elements between reception and transmission, while protecting the signal processors connected to the acoustic transducer elements. The transceiver circuitry 700 includes multiple transmit sections, one of which is labeled 702 that incorporates a transmit section input 704, a transmit section output 706, and the two sets of receive signal blocking circuitry disposed between the transmit section input 704 and the transmit section output 706. As shown in FIG. 7, the receive signal blocking circuitry includes the back-to-back diode D1; and the back-to-back diode D3 coupled to the capacitor Cshunt.

The transceiver circuitry 700 also includes multiple receive sections, one of which is labeled 708 that incorporates a receive section output 710, a receive section input 712, and two sets of transmit signal blocking circuitry disposed between the receive section input 712 and the receive section output 710. The transmit signal blocking circuitry includes the capacitor Ccoupl connected to the diode D2; and the back-to-back diode D4 connected to the capacitor C2. The receive section inputs 712 are receive signal connections that transport receive signals obtained form the transducer elements to the signal processor 110.

The acoustic transducer elements are coupled to the transmit section output 706 and the receive section input 712. The transmit section output 706 and the receive section input 712 are connected together at the transducer elements, one of which is labeled E in FIG. 7. Similarly, the transmit section input 704 and the receive section output 710 are connected together. The receive section output 710 acts as a receive sub-aperture output driven by the signal processor 110 in the receive direction. The receive sub-aperture output thus carries a signal obtained over a receive sub-aperture, for example, a beamformed receive signal formed from receive signals obtained from 15 transducer elements in a triangular receive sub-aperture.

Note that each transmit section 702 is coupled to four transducer elements E through four diodes D1. The four transducer elements form the 2×2 transmit sub-aperture explained above. Similarly, fifteen transducer elements E are combined and summed into one receive sub-aperture output channel. Each of the fifteen receive section inputs 712 for a given receive sub-aperture includes the capacitor Ccoupl and diode pair D2. On the output side, each of the receive section outputs 710 for the combined signal obtained over the receive sub-aperture includes the diode pair D4 and the capacitor C2.

The transceiver circuitry 700 permits the transducer elements E to be multiplexed between signal reception and signal transmission while protecting the inputs and outputs of the signal processor 110. In other words, any given transducer element E may be employed to both transmit acoustic energy and receive acoustic energy.

It might not be desirable to multiplex every transducer element E, however. If some of the transducer elements in the array 300 are used for reception only, a transducer element E need not have a transmit section 702 coupled to it. This is shown in FIG. 7 and the receive only elements labeled 714 and 716. Furthermore, the transmit signal blocking circuitry may be omitted for a receive only transducer element. Similarly, a transducer element E employed only in the transmit direction need not have a receive section 708 coupled to it, nor include the receive signal blocking circuitry. Thus, for example, the receive signal blocking circuitry labeled 718 (as well as Ccoupl and D2) may be omitted for a transmit only channel.

In operation, the transmit signal (e.g., a 100 volt pulse) coming from the host system 116 passes through the diodes D3, the tuning inductor $L_{tuning}$ and the diodes D1 to drive the transducer elements E. After the tuning inductor, the transmit signal splits into four signals and passes through four sets of D1 diodes to the four transducer elements that make up a 2×2 transmit sub-aperture.

As shown in FIG. 7, the diodes D1, D2, D3, D4 appear as antiparallel pairs. The voltage drop on the diodes is small compared to the transmit voltage and do not have a significant impact on the transmit signal during transmit. The tuning inductor is selected to provide a voltage step-up to the transducer elements E. The resonance frequency of that circuit (i.e., the tuning inductor and the effective capacitance) is tuned to match the desired transmit frequency. The effective capacitance is formed by the parallel components of transducer element, the parasitic shunt capacitance and the coupling capacitor $C_{coupl}$.

The coupling capacitor $C_{coupl}$ protects the signal processor 110 inputs from the transmit signal voltage. The signal processor 110 includes the internal clamping diodes D2 which provide the current to charge the coupling capacitor to the transmit voltage. Thus, the coupling capacitor takes up nearly all of the transmit voltage, while the diodes D2 hold the voltage present at the signal processor 110 input at plus or minus one diode drop (e.g., 0.7 V).

Because the coaxial cables 122 mainly are used for both transmit and receive, the transmit waveform would also appear (without the transmit blocking circuitry) at the signal processor 110 output. The capacitor $C_2$ and diodes D4 protect the signal processor 110 output from the transmit voltage. Specially, D4 clamps the signal to one diode drop while $C_2$ decouples the signal processor 110 output from the transmit waveform by taking up the majority of the transmit voltage. The transmit waveform is sufficiently filtered by the coaxial cable 122 to limit the charge current for the capacitors $C_2$ and $C_{coupl}$.

During receive, the receive signals from the transducer elements E pass through $C_{coupl}$ to the signal processor 110. The signal processor 110 input stage is a charge amplifier A with gain determined by $C_{coupl}$. In general, for a good noise figure, the impedance of the coupling capacitor should be small compared to the impedance of the transducer element E. However, a small impedance value increases the charge current during transmit.

Because the voltage on the transducer element is small during receive, the diodes D1 are open. The diodes D1 thus operate as a low voltage signal blocker to decouple the transducer elements E from each other. The echo signals received from the transducer elements are delayed and summed inside the signal processor 110 and provided to the receive section output 710. More specifically, the output signal passes through the output resistor R and the capacitors C1 and C2 to the coaxial cable 122. The load from the host system 116 preamplifier and the coaxial cable 122 capacitance is large enough to limit the output voltage at D4 to be less then the diode on-voltage. Thus, the diodes D4 are open-circuit during receive.

The resistor R effectively controls the signal gain into the coaxial cable 122. The value of the protection capacitor C2 (similar to the input coupling capacitor) is a trade-off between transmit surge current and receive impedance. In one implementation, the capacitor C2 is approximately 100 pf. The capacitor C1 decouples the output DC level from the clamping diodes D4. The precise value for C1 is not critical, but may be set to be several times the value of C2 (e.g., 1 nf) in order to avoid signal reduction due to C1.

The shunt capacitor Cshunt reduces the crosstalk from the receive section output 710 back to the receive section input 712. More specifically, even though the diodes D3 are in the off state during receive, their parasitic capacitance in the pF range will create crosstalk. The shunt capacitor is large compared to the parasitic capacitance and presents a much lower impedance than the parasitic capacitance. As a result, the diode D3 and shunt capacitor create a voltage divider where the majority of the voltage drops off at the parasitic capacitance, while the shunt capacitor takes only a small voltage drop. Thus, the small voltage on the shunt capacitor effectively limits cross talk. Note that during transmit, when the diodes are essentially short-circuits, the shunt capacitor is a negligible load compared to the coaxial cable 122 capacitance.

Figure 8:
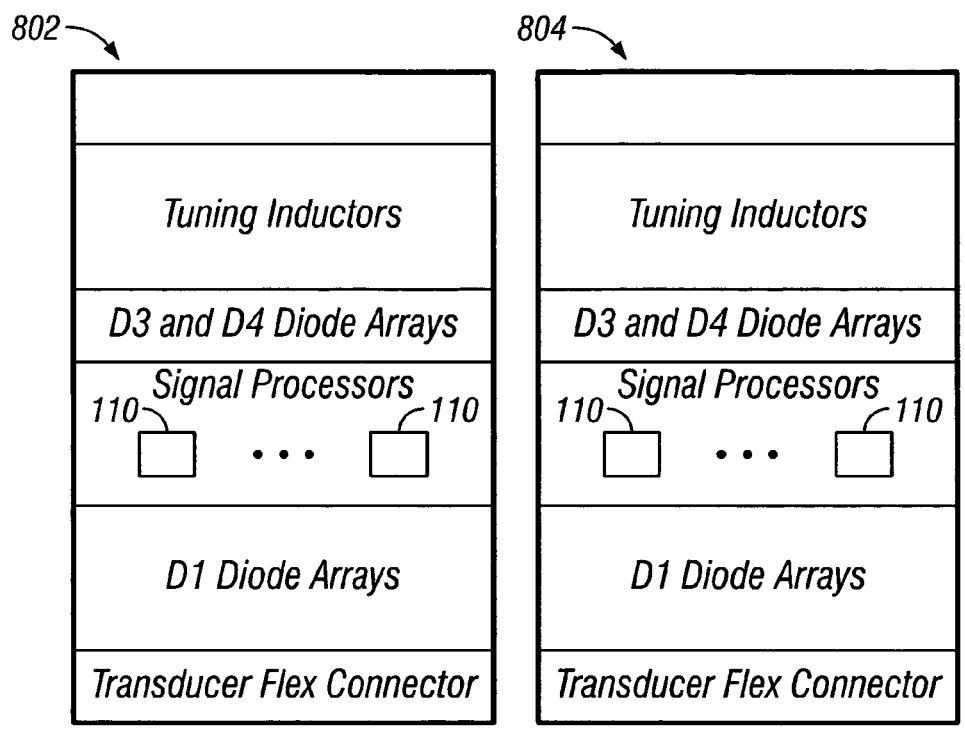
FIG. 8 shows the front side and the back side of a processing board, including suggested layout areas for the electronics carried by the processing board.

FIG. 8 shows the bottom layer 802 and top layer 804 side of a processing board 106. FIG. 8 shows an exemplary layout plan for the processing electronics included on each processing board 106 as described in detail above with regard to FIG. 7. As shown in FIG. 8, the signal processors 110 may occupy the central area of the processing boards, while the D1 diode arrays may be located below the signal processor 110 and the D3 and D4 diode arrays may be located above the signal processors 110.

Figure 9:
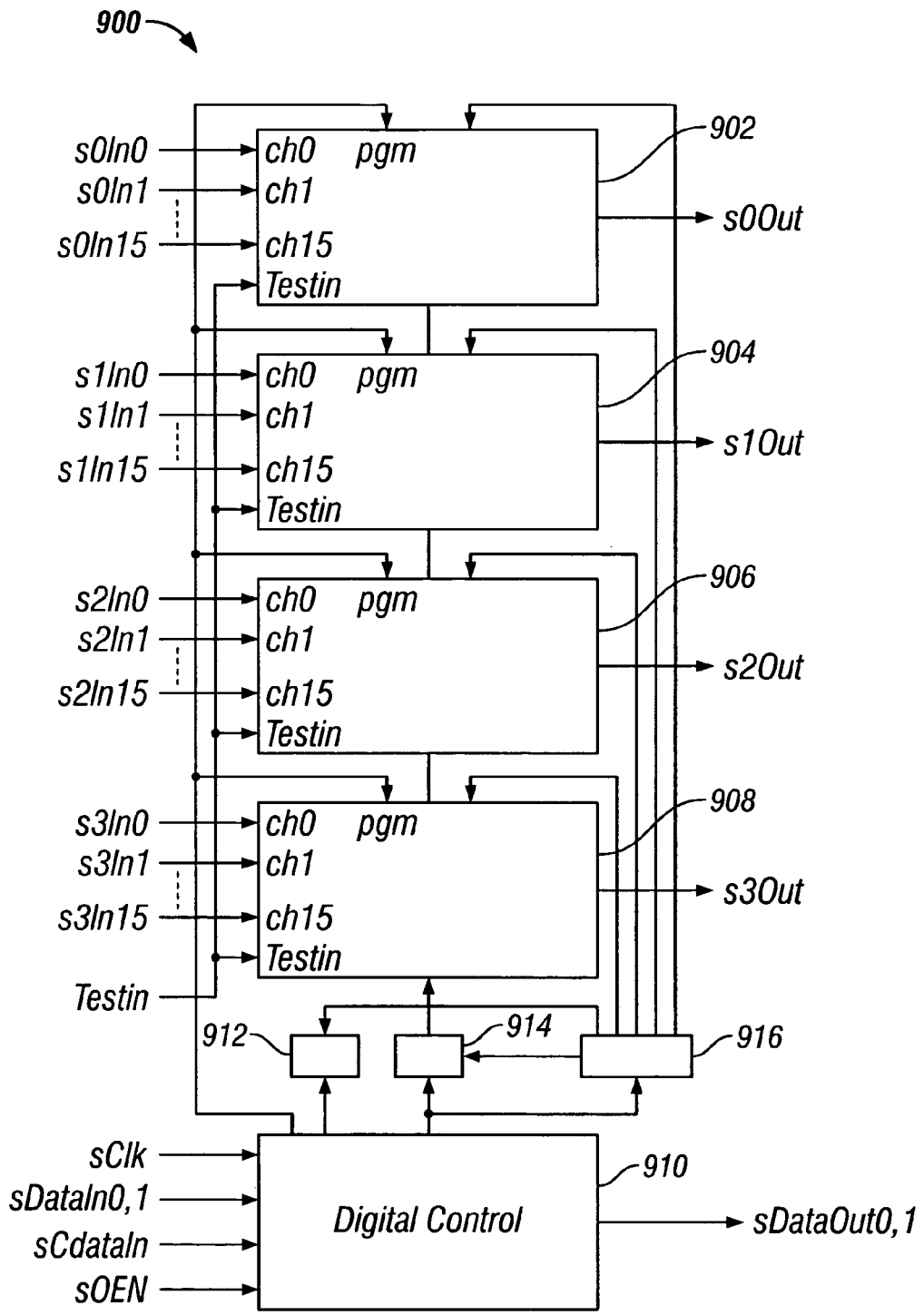
FIG. 9 depicts a block diagram of a signal processor suitable for use with the ultrasound probe shown in FIG. 1.

Turning next to FIG. 9, that figure shows a block diagram 900 of a signal processor 110. The signal processor 110 includes four aperture processors 902, 904, 906, and 908, a digital control block 910, and support circuitry that may include a delay tuning circuit 912, a recovery voltage circuit 914, and a bias circuit 916.

Each aperture processor 902-908 includes sixteen receive inputs (e.g., s0In0-soIn15) that are connected to transducer elements that form a receive sub-aperture. In one embodiment, the receive sub-aperture is triangular and formed from fifteen transducer elements. Thus, one input on each sub-aperture processor 902-908 may go unused. Each sub-aperture processor 902-908 also includes a test input (labeled testin) and digital control inputs (labeled pgm). The sub-aperture processors 902-908 perform beamforming on the receive input signals and output the beamformed signal obtained over the receive sub-aperture on the receive sub-aperture outputs (labeled s0ut-s3Out).

The digital control block 910 includes clock (sClk, e.g., a 20 MHz system clock), data (sDataIn0 and 1, serial data inputs and sCdataIn, a serial control data input), and control (sOEN, an output enable for the signal processor 110) signals. The digital control block also includes two data outputs (sDataOut0 and 1). The data inputs and outputs may be used to chain signal processors 110 in series as noted below.

Figure 10:
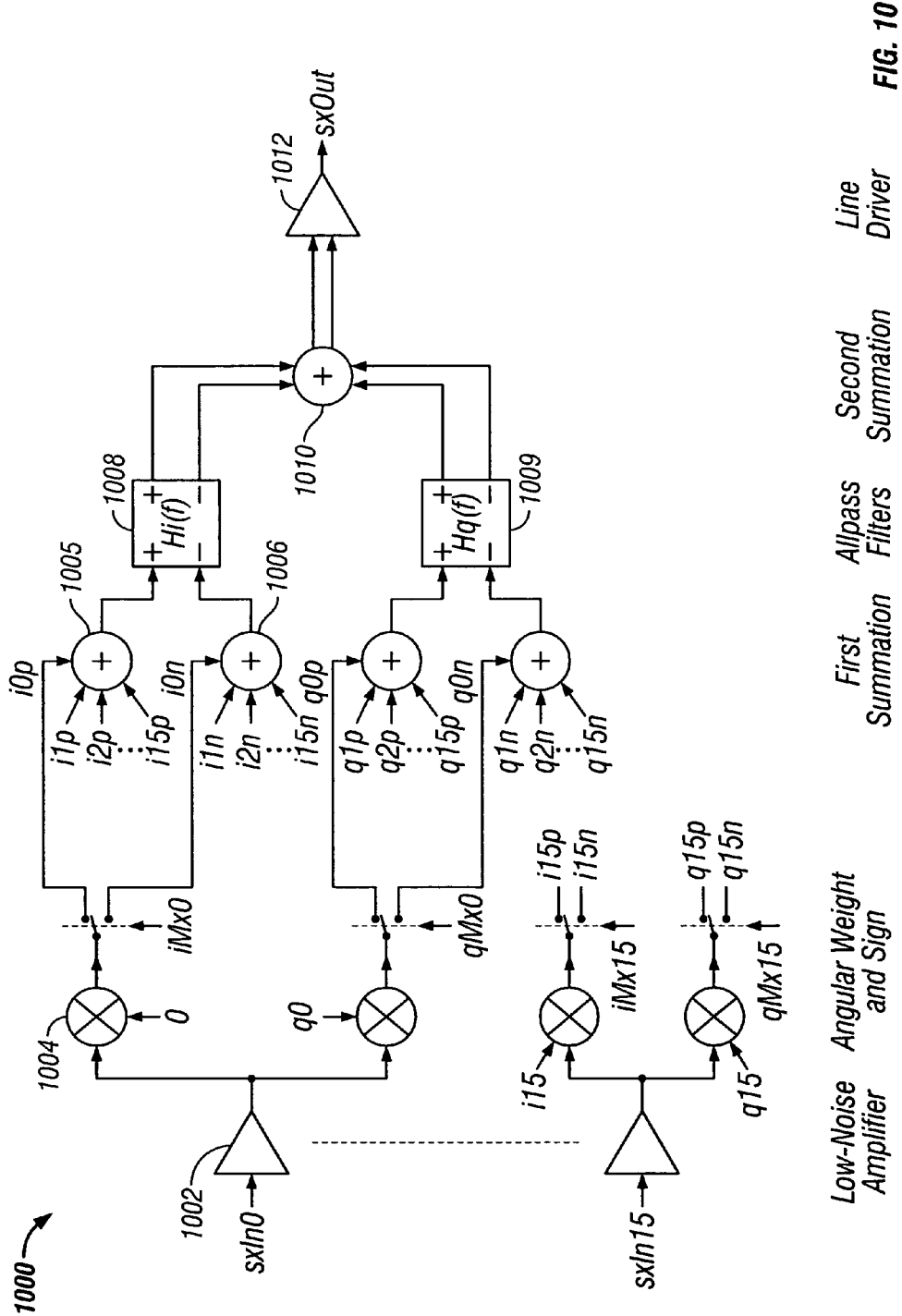
FIG. 10 shows narrowband beamforming circuitry in the signal processor.

The circuitry in the signal processor 110 is described in more detail below with regard to FIG. 10. FIG. 10 shows the narrowband beamforming circuitry 1000 in the signal processor 110. Each receive input (one of which is labeled sxIn0) passes through a low-noise amplifier 1002, a weighting and summation stage including mixers (one of which is labeled 1004), summers (a positive summation summer labeled 1005 and a negative summation summer labeled 1006), and all-pass filters 1008 and 1009. In addition the all-pass filters connect to second summers (one of which is labeled 1010) and through a line driver 1012 out to the receive sub-aperture output (one of which is labeled sxOut).

The low-noise amplifiers (LNA) are charge sensitive amplifiers that amplify the receive signal from a transducer element via the external coupling capacitor. The LNA gain may be set by adjusting the ratio between the external coupling capacitor and an internal feedback resistor. Typically the open loop gain for the LNA is high, while typical closed loop gain (at 3 MHz) is selected to exploit the available signal range.

The LNAs have fast recovery time in part due to the recovery voltage circuit 914. If the receive signal voltage drive the circuitry into saturation recovery circuitry is activated to ensure fast recovery from the input stage saturation.

As shown in FIG. 10, Inphase (I) and Quadrature (Q) signals are generated from the receive signals. To that end, each input is given weight and sign depending on the desired channel delay before all the inputs are summed. A multi-input amplifier does the weighting and summing by employing individually selectable input capacitor sizes on each input. A fully differential amplifier may be employed for the summation. The sign of each input is set by feeding the input either to the positive summation node 1005 or negative summation node 1006.

In one embodiment, the signal processor 110 uses the following weights shown in Table 2 and Table 3 for 22.5 degree quantization.

TABLE 2

| Phase | IMx | qMx |
|---|---|---|
| 0 <= phase < Pi/2 | 1 | 1 |
| Pi/2 <= phase < Pi | −1 | 1 |
| Pi <= phase < 3Pi/2 | −1 | −1 |
| 3Pi/2 <= phase < 2Pi | 1 | −1 |

TABLE 3

| Phase | In | qn |
|---|---|---|
| 0 | 1 | 0 |
| pi/8 | 0.924 | 0.383 |
| pi/4 | 0.707 | 0.707 |
| 3Pi/8 | 0.383 | 0.924 |
| Pi/2 | 0 | 1 |
| X | 0 | 0 |

The summation stage 1010, having the second summers, may further include an attenuation to level the signal swing of the available range.

The all-pass filters impart, to the I and Q signals, phase delays chosen to minimize differential phase error over a frequency band of interest. Each filter has a first-order transfer function given in the s-plane by $H(s)=(1-st)/(1+st)$, where t is the RC time constant of the filter. The transfer function may be realized using resistors and cross-coupled capacitors with active feedback. More specifically, the all-pass filters may be implemented as a non-inverting buffer followed by a resistor, in parallel with an inverting buffer in series with a capacitor (See FIG. 20).

In one embodiment, the all-pass filter 1008 has RC=25 ns, and the all-pass filter 1009 has RC=145 ns at 3 MHz. The determination of iMx, qMx, in, and qn are described below with regard to FIG. 15 and Table 4.

The line driver 1012 drives the beamformed receive signal back to the host system 116. The line driver 1012 may use a opamp with a very large output stage connected as a combination of a summer and difference amplifier. In this fashion, the signal from the I and Q channels are summed and converted into a single ended output. The gain of the combined second summation stage and line driver are selected to give the desired output range.

The delay tuning circuitry 912 is included to account for variations in process and operating conditions that may alter the time constants of the allpass filters. To control the time constants, the tuning circuit 912 is included.

The bias circuit 916 controls the bias currents to the analog modules in the signal processor 110. The power supply voltage may be used as a reference voltage. In one implementation, the bias current is distributed over the signal processor 110 to supply the different analog modules with the required bias current.

Figure 13:
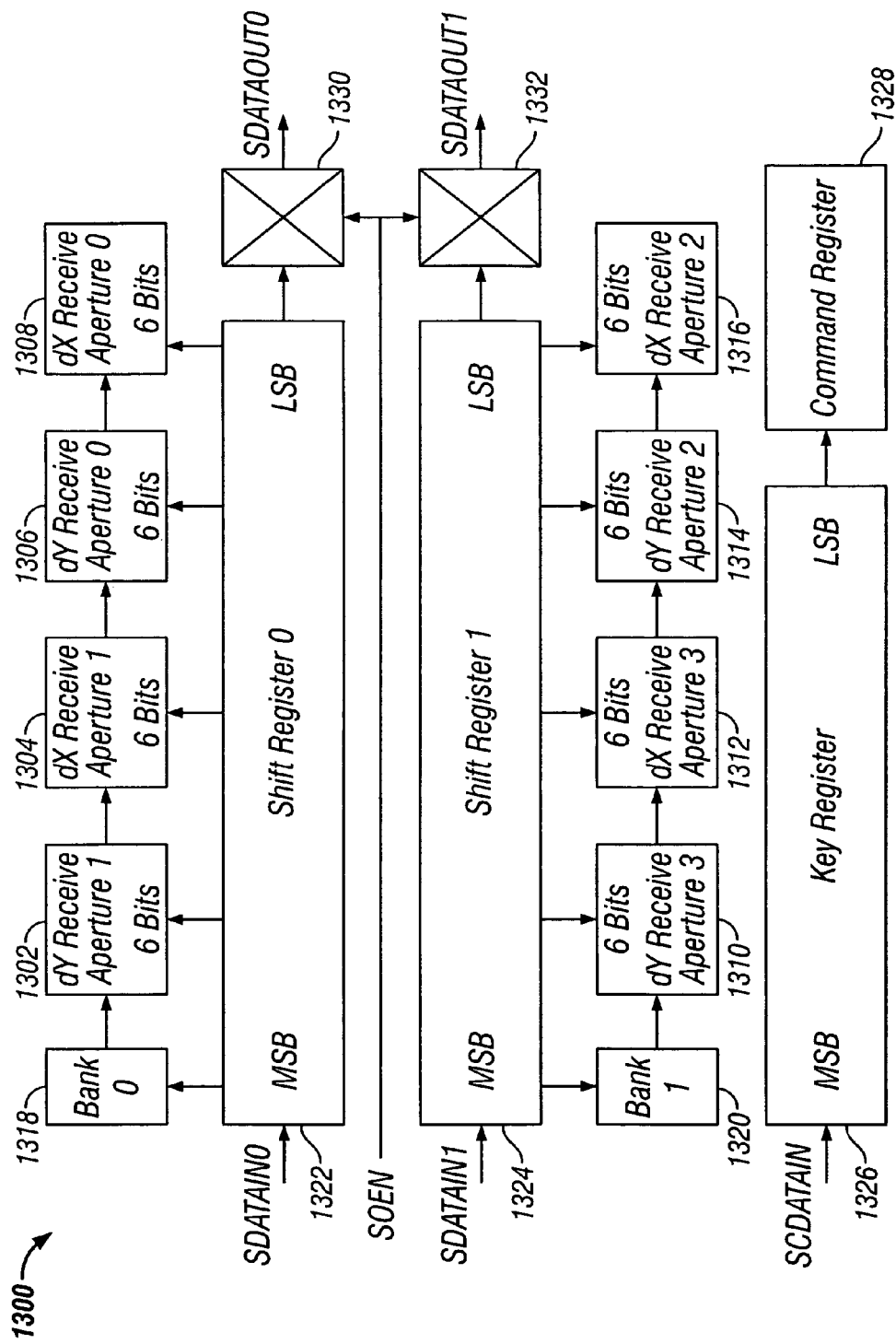
FIG. 13 shows a block diagram of a digital interface for the signal processor.

Turning next to FIG. 13, that figure shows a block diagram of the digital interface 1300 of the signal processor 110 that is included in the digital control block 910. The digital interface 1300 includes four pairs of six-bit registers/memories 1302 and 1304, 1306 and 1308, 1310 and 1312, and 1314 and 1316 for storing delta Y and delta X inclination parameters for the four receive apertures handled by the signal processor 110. The digital interface 1300 also includes two 1-bit bank memories 1318, 1320, two data shift registers 1322, 1324, a multi-bit key register 1326, and a multi-bit command register 1328. The tri-state buffers 1330 and 1332 allow the interface 1300 to place its outputs in a high impedance state under control of the SOEN signal.

The interface 1300 may be used to program, set up and read from the signal processor 110. The interface 1300 includes a command line (SCDATAIN), two data lines (SDATAIN0, 1), one enable line (SOEN), and one clock line SCLK (not shown). The SDATAIN0 and SDATAIN1 lines provide for serial data input to the two data shift registers 1322, 1324 (labeled SHIFTREGISTER0, 1), while SCDATAIN provides for serial data input to a control data shift register. In one implementation, the data shift registers may be 25 bits long, while the control shift register may be 36 bits long.

The signal processor 110 is typically used in a hostile environment where the digital input lines are expected to assume random values during ultrasound-transmission. To avoid getting false data and commands through the digital interface, the 32 bit key register is used as an enable signal. When the correct key resides in the key register (compared to the key pre-selected and pre-set in the signal processor 110), the digital controller executes the command placed in the 4 bit command register.

The data lines may be shifted simultaneously into the registers controlled by the SCLK data clock. SCLK runs, for example, at 20 MHz. Note that the interface 1300 also includes two digital outputs labeled SDATAOUT0 and SDATAOUT1. These outputs are the outputs of the data shift registers and may be used to connect multiple signal processors 110 in a chain (See FIG. 14). Output data from the signal processors 110 are shifted through the serial chain and read out from the last signal processor 110 in the chain.

Because the output-bus is connected to the input-bus in the chain, the SOEN signal may be employed to place the output of the last signal processor 110 in tristate mode (Hi Z mode) when writing to the chain. When reading out data over the serial bus, SOEN may be used to enable the output from the last signal processor 110.

In one implementation, the 36-bit control data register includes of a 32-bit key register and a 4-bit command register. The SCDATAIN line may be a separate signal line to all signal processors 110 on a processor board 106. In addition, as shown in FIG. 13, the serial shift registers are shifted in from most significant bit (MSB). In other words, command and data is shift in LSB first.

Also shown in FIG. 13 are the six bit inclination parameter memories that store location information for the four receive sub-apertures handled by the signal processor 110. The pair of six-bit memories 1302, 1304 store delta Y and delta X inclination information for a receive sub-aperture and the pair of six-bit memories 1306, 1308 store delta Y and delta X inclination parameters for a second receive sub-aperture. Similarly, the pair of six-bit memories 1310, 1312 store delta Y and delta X inclination parameters for a third receive sub-aperture and the pair of six-bit memories 1314, 1316 store delta Y and delta X inclination parameters for a fourth receive aperture. Then loading the signal processor static information (geometry ram, setup registers, encoder ram, etc.) the shift register division is adapted to the data loaded.

Figure 14:
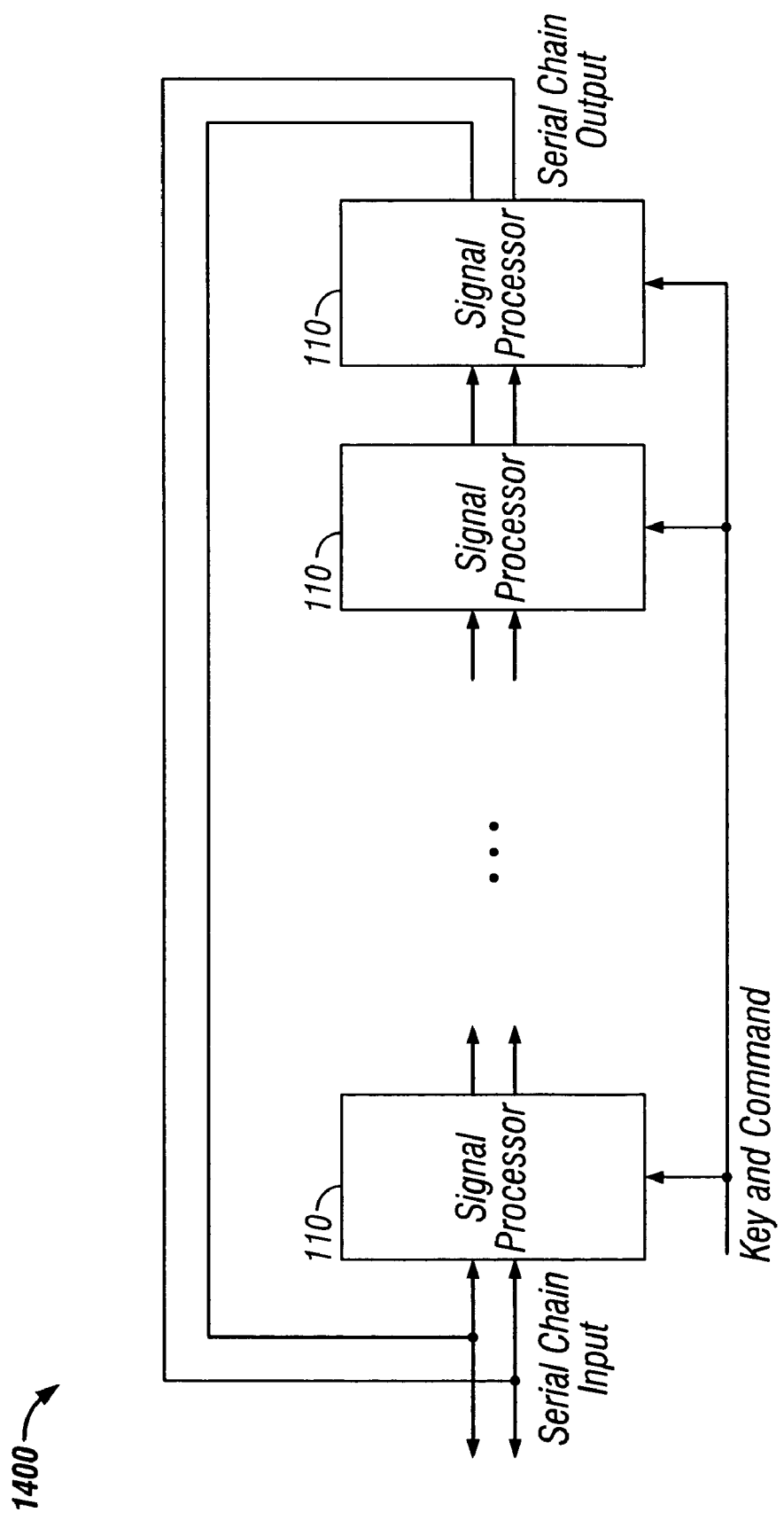
FIG. 14 shows signal processors connected in a serial chain.

Turning briefly to FIG. 14, that figure shows a serial chain 1400 of signal processors 110. The serial chain 1400 is connected through the SDATAOUT0, SDATAOUT1, SDATAIN0, and SDATAIN1 signal lines. A clock line, latch line, and parameter selection line (for selecting which parameter registers to write) may also be provided.

Figure 15:
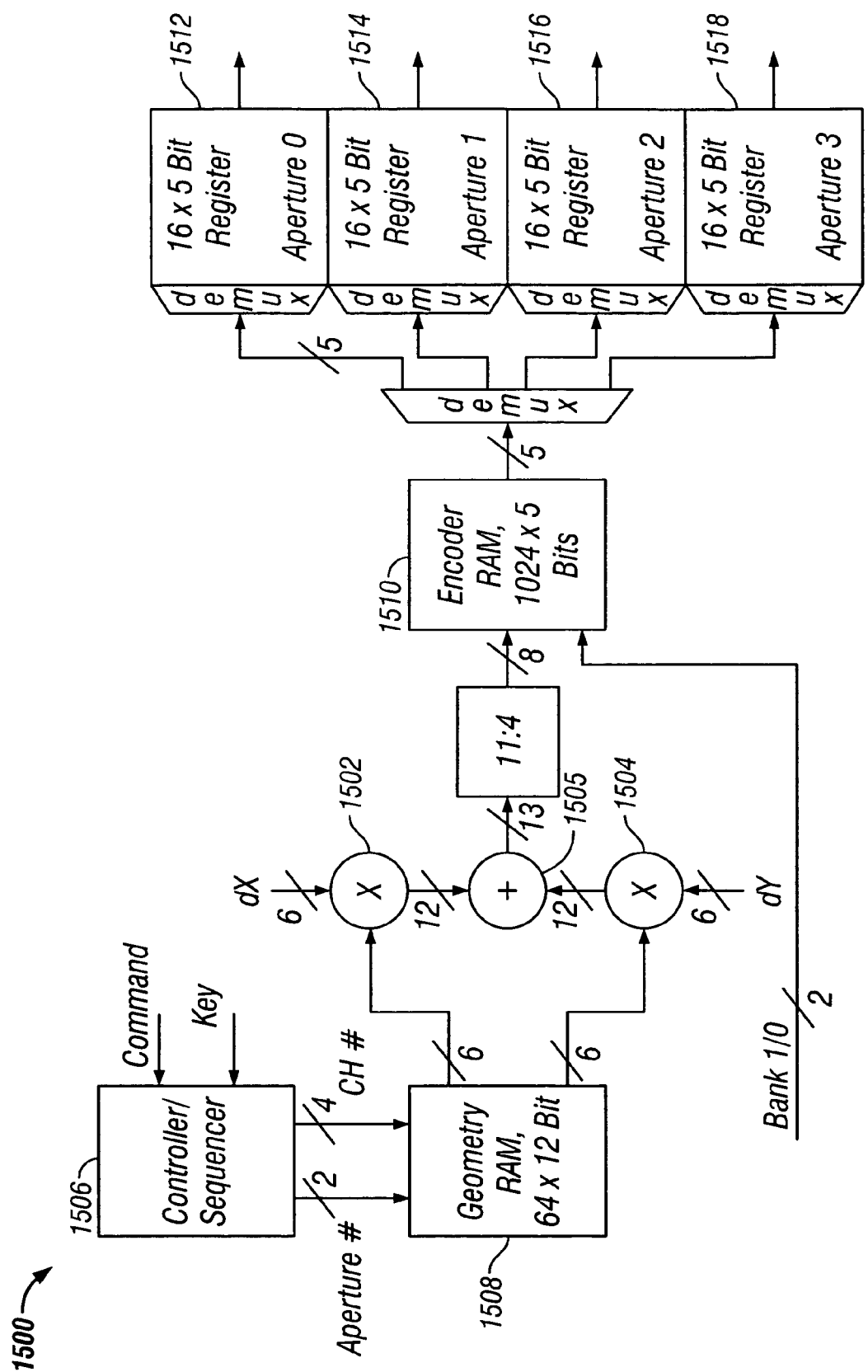
FIG. 15 shows a cross-point controller in the signal processor that calculates new control values for processing the four receive sub-apertures assigned to the signal processor.

Turning next to FIG. 15, that figure shows a cross-point controller 1500 in the signal processor 110 that calculates new control values for processing the four receive sub-apertures assigned to the signal processor 110 based on the delta X, delta Y inclinations loaded through the serial interface (See FIG. 13). The cross-point controller 1500 will calculate 16 new delay settings for each aperture, based on new inclinations parameters delta X, delta Y. The delay setup are calculated based on the contents of the geometry RAM and the new inclinations parameters delta X, delta Y. The corresponding phase delays are found from lockup in the chosen encoder RAM bank.

To that end, the cross-point controller 1500 includes the multipliers 1502, 1504, and a summer 1505. The cross-point controller 1500 also includes a controller 1506, a geometry ram 1508, and an encoder ram 1510. Four sets (one for each receive sub-aperture) of sixteen 5-bit phase setting registers 1512, 1514, 1516, and 1518 are provided (a total of 64 five-bit registers). These delay setting registers store the delay setting control bits for each receive sub-aperture handled by the signal processor 110, as noted below.

The geometry RAM 1508 holds the relation between a receive signal channel n, and the corresponding transducer location $(x_n, y_n)$ within the receive sub-aperture. The encoder RAM 1510 holds the relation between the coded delay and the hardware settings (iMxn, in, qMxn, qn) shown in FIG. 10 for narrowband beamforming. Alternatively, the encoder RAM 1510 holds the relation between the desired delay and the cross-point switch control signals intPol, chPos(4), and sign for the broadband beamforming circuitry shown in FIG. 19. The parameter delta Xn represents the x-inclination for sub-aperture n, n=0, 1, 2, 3, while delta Yn represents the y-inclination for sub-aperture n, n=0, 1, 2, 3 for each of four sub-apertures handled by the processor 110.

When a valid key is detected in the key register and the start cross-point calculation command is selected, the cross-point controller 1500 calculates new register values for sub-apertures 0, 1, 2 and 3. Because up to 16 receive signals may contribute to each receive aperture, a total of 64 calculations are performed. The delta X and delta Y values shown in FIG. 15 are the values loaded from the serial interface prior to each new setup. All eight delta X and delta Y values loaded during the previous setup calculation are available to the cross-point controller 1500 via two 24 bit buses as shown in FIG. 13.

To save setup time, the data to be used in the next calculation is shifted in and loaded while the signal processor is calculating the current setup. When the current calculation is finished, the new delta X and delta Y data have been loaded and are ready for the next setup calculation.

To start a calculation the key and command register are loaded with the key value and the bit code assigned to the desired command. When a calculation is initiated, delta X and delta Y values for aperture 0 are put on the multiplier 1502, 1504 inputs. A sequencer 1506 controls the calculations. The sequencer 1506 may be implemented as an up counter that cycles through all 64 receive signal inputs (4 sub-apertures times 16 receive inputs per sub-aperture). The sequencer 1506 is connected to the address bus of the geometry RAM 1508. The data for one sub-aperture is generally calculated before advancing to the next sub-aperture.

The sequencer 1506 also controls routing the signal from the encoder RAM 1510 to the correct analog sub-aperture register 1302-1314, as well as the multiplexing of the correct delta X and delta Y data to the cross-point controller 1500. In one implementation for narrowband beamforming, the output from the Encoder RAM 1510 is a 5 bit word, called sap_data [4:0] that maps to sX_m_controlX( ).

sX_m_controlX( ) maps to the control signals for the beamforming circuitry shown in FIG. 10. The five bits sX_m_control4 . . . 0(Y) directly control the angular weight and sign to the Y channel (receive signal) for aperture X. The translation from bit values to angular weight and sign is given in Table 4. In other words, the Encoder RAM 1510, for narrowband beamforming, maps from a delay value to the multiplexer sign (iMxn and qMxn) and the I and Q scaling (in and qn). These parameters implement 16 phase angles, and to be able to omit signals with given delays, in=qn=0 may also be selected. As a result, the word length in the Encoder RAM 1510 is 5 bits. Alternatively, the bits in the Encoder RAM 1510 may directly choose coefficients and multiplexer values (e.g., using one bit for each multiplexer, and 3 bits with decoder to select each of the six gain-pairs in Table 3).

TABLE 4

Mapping between SAP control bits and phase

| # | bit4 | bit3 | bit2 | bit1 | bit0 | iMxn | in | qMxn | qn | Phase |
|---|------|------|------|------|------|------|------|------|------|--------|
| 0 | 0 | 0 | 0 | 0 | 0 | 1 | 1.0 | X | 0.0 | 0 |
| 1 | 0 | 0 | 0 | 0 | 1 | 1 | 0.924 | 1 | 0.383 | Pi/8 |
| 2 | 0 | 0 | 0 | 1 | 0 | 1 | 0.707 | 1 | 0.707 | Pi/4 |
| 3 | 0 | 0 | 0 | 1 | 1 | 1 | 0.383 | 1 | 0.924 | 3Pi/8 |
| 4 | 0 | 0 | 1 | 0 | 0 | X | 0.0 | 1 | 1.0 | Pi/2 |
| 5 | 0 | 0 | 1 | 0 | 1 | −1 | 0.383 | 1 | 0.924 | 5Pi/8 |
| 6 | 0 | 0 | 1 | 1 | 0 | −1 | 0.707 | 1 | 0.707 | 3i/4 |
| 7 | 0 | 0 | 1 | 1 | 1 | −1 | 0.924 | 1 | 0.383 | 7Pi/8 |
| 8 | 0 | 1 | 0 | 0 | 0 | −1 | 1.0 | X | 0.0 | Pi |
| 9 | 0 | 1 | 0 | 0 | 1 | −1 | 0.924 | −1 | 0.383 | 9Pi/8 |
| 10 | 0 | 1 | 0 | 1 | 0 | −1 | 0.707 | −1 | 0.707 | 5Pi/4 |
| 11 | 0 | 1 | 0 | 1 | 1 | −1 | 0.383 | −1 | 0.924 | 11Pi/8 |
| 12 | 0 | 1 | 1 | 0 | 0 | X | 0.0 | −1 | 1.0 | 3Pi/2 |
| 13 | 0 | 1 | 1 | 0 | 1 | 1 | 0.383 | −1 | 0.924 | 13Pi/8 |
| 14 | 0 | 1 | 1 | 1 | 0 | 1 | 0.707 | −1 | 0.707 | 7Pi/4 |
| 15 | 0 | 1 | 1 | 1 | 1 | 1 | 0.924 | −1 | 0.383 | 15Pi/8 |
| 16...31 | 1 | X | X | X | X | X | 0.0 | X | 0.0 | X |

The calculations may be done with 2's complement number representation. Referring again to FIG. 15, the delta X and delta Y and geometry RAM data are multiplied and summed in the summer 1505. This calculation produces a 13 bit output. Because delta X and delta Y are never maximal at the same time, in the calculations the two MSBs will always be the same and the MSB of the signal can be truncated. In the implementation shown in FIG. 15, precision is reduced to 8 bits by truncating the four LSBs.

The cross-point controller 1500 sequences through all transducer element receive inputs 'n' for every receive aperture 'm' handled by the signal processor 110. The cross-point controller 1500 may be considered to determine a scaled version of the delay to be introduced to each receive signal as: floor((x(m,n)*deltaX(m)+y(m,n)*deltaY(m))/16), for n=0, 1, ... 15, and m=0, 1, 2, 3.

Note that x(m,n) and y(m,n) are the geometrical positions of the transducer element coupled to the nth input for receive aperture m. The positions are indexed through the geometry RAM 1508 to add routing flexibility during processing circuit board 106 layout. The inclination parameters deltaX(m) and deltaY(m) may remain constant for all receive signals in a given receive sub-aperture m, but may typically vary between the sub-apertures.

The calculated delay is converted into a physical delay through a table look-up in the encoder RAM 1510.

With regard to the geometry RAM 1508, it takes a 6 bit address and stores 12 bit data. To start loading data to the geometry RAM 1508, the command RESET_ADDR_COUNTERS is issued to reset the address counters. The next command is then LOAD_GEOM_RAM, which will write data to the current addresses pointed to by the address counter, and auto-increment the address counter. Because the datawidth is 12 bit, one shift/load procedure will load 4 datawords into the geometry RAM 1508. The address counter will therefore be incremented by 4 at each load.

The encoder RAM 1510 is divided into four banks, reflecting four different frequency settings for the ultrasound probe 100. The bank0 and bank1 registers loaded from the serial interface specify which bank is used. Together with the eight bits from the calculation, they make up the encoder RAM address in the 1024x 5 bit RAM.

The encoder RAM 1510 has a 10 bit address bus and a 5 bit data bus. To start loading data to encoder RAM 1510, the command RESET_ADDR_COUNTERS is issued to reset the address counters. The next command is LOAD_ENC_RAM, which will write data to the current addresses pointed to by the address counter and bank 0/1 registers, and auto-increment the address counter. Since the data width is 5 bit, one shift/load procedure will load 8 aperture control data words to the RAM 1510. The address counter will therefore be incremented by 8 at each load.

Bits [19:0] in both serial shift registers are used for data to the RAMs. Bit 24 of serial shift register 0 is mapped to the bank 0 control signal for the encoder RAM 1510, and bit 24 of serial shift register 1 is mapped to the bank 1 control signal. Bank 0/1 registers (See FIG. 13) control which bank is loaded. In one embodiment, the location memory controller 112 sends four—bit commands to the signal processors 110. The commands are shifted into the signal processors 110 into the command register 1328. Exemplary commands are presented below in Table 5:

TABLE 5

| Name | Command |
|------|---------|
| RESET | Places the signal processor into a known state |
| LOAD_X_Y_Data | Load delta X and delta Y and encoder bank from shift register. |
| RESET_ADDR_COUNTERS | Reset all address counters for reading and writing to the signal processor. |
| LOAD_GEOM_RAM | Load 4 datawords to geometry RAM. |
| LOAD_ENC_RAM | Load 8 datawords to encoder RAM. |
| CALCULATE | Calculate new aperture beamforming values. |
| DELAY_TUNING_START | Start analog tuning and calibration procedure. |
| WRITE_ANALOG_MP_REG | Write to the analog multi-purpose register in the signal processor. |
| READ_ANALOG_MP_REG | Put the analog multi-purpose register, containing, for example, the delay measurement from the delay tuning, on the 1322, 1324. |
| READBACK_REGS | Read out the internal registers of the signal processor. |
| WRITE_REGS | Write directly to the internal registers of the signal processor. |
| LOAD_PD_REG | Write a analog power-down register. |

Figure 16:
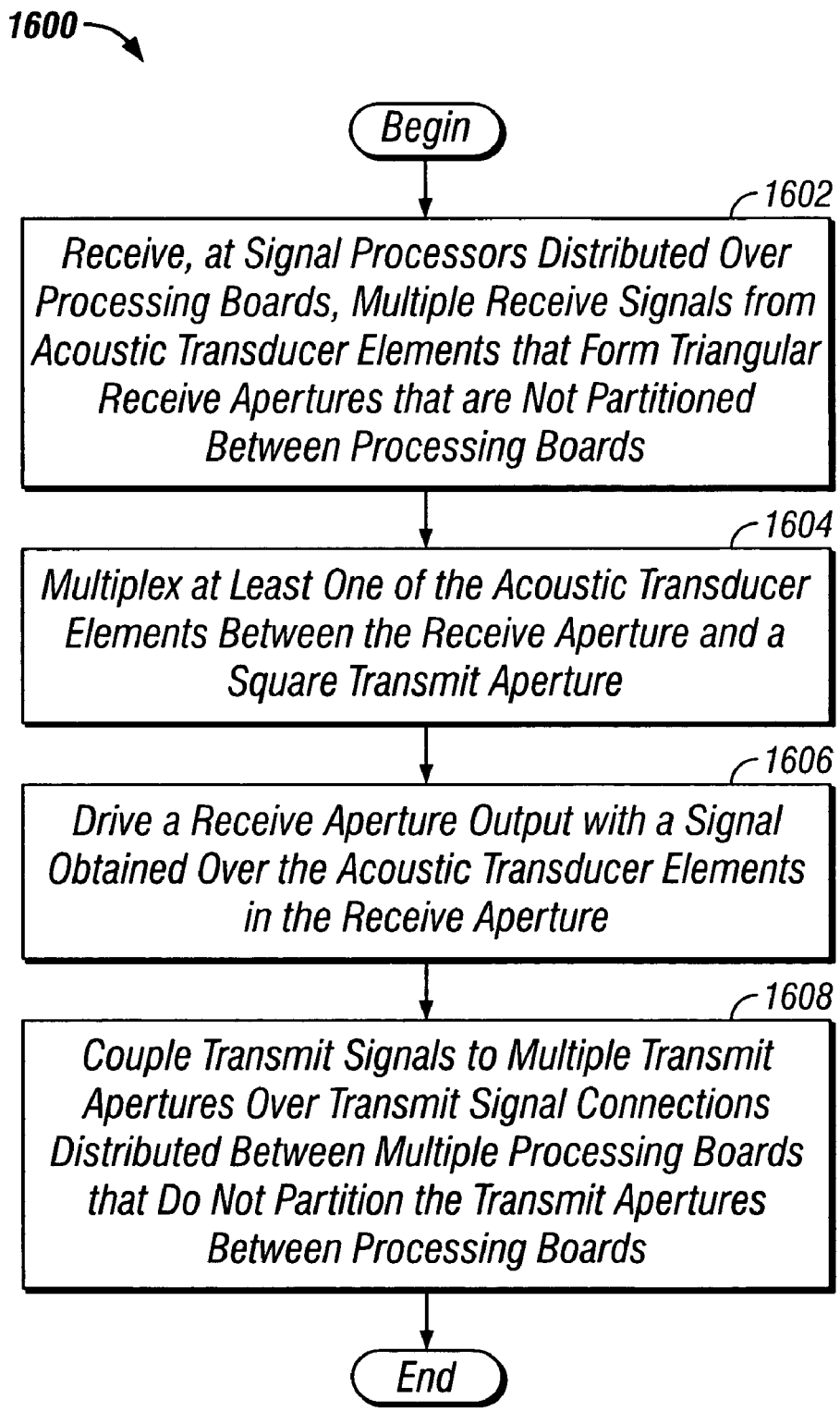
FIG. 16 shows steps that the ultrasound probe shown in FIG. 1 may take to perform sub-aperture processing.

FIG. 16 summarizes the steps 1600 that the ultrasound probe 100 shown in FIG. 1 may take to perform sub-aperture processing. The probe 100 receives, at signal processors 110 distributed over processing boards 106, multiple receive signals from acoustic transducer elements (Step 1602). The transducer elements may form triangular receive sub-apertures that are wholly processed by a given signal processor 110, rather than being partitioned between processing boards. During the receive (and transmit) operations, the probe 100 multiplexes at least one of the acoustic transducer elements between the receive sub-aperture and a square transmit sub-aperture (Step 1604).

After beamforming, the signal processor 110 drives a receive sub-aperture output with a beamformed signal obtained over the acoustic transducer elements in the receive sub-aperture (Step 1606). In the transmit direction, the probe may couple transmit signals to multiple transmit sub-apertures over transmit signal connections distributed between multiple processing boards (Step 1608). Like the receive apertures, the transmit signal connections for a given sub-aperture may all be provided on a given processing board 106, rather than being partitioned across multiple processing boards 106.

Not partitioning the transmit or receive sub-apertures between multiple processing boards provides for efficient routing of signals between the host system 116 and the processing boards 106 to the transducer array 102. Because each processing board 106 processes its own transmit and receive sub-apertures, no cross-connecting signals or routing needs to be provided between the processing boards 106.

Figure 17:
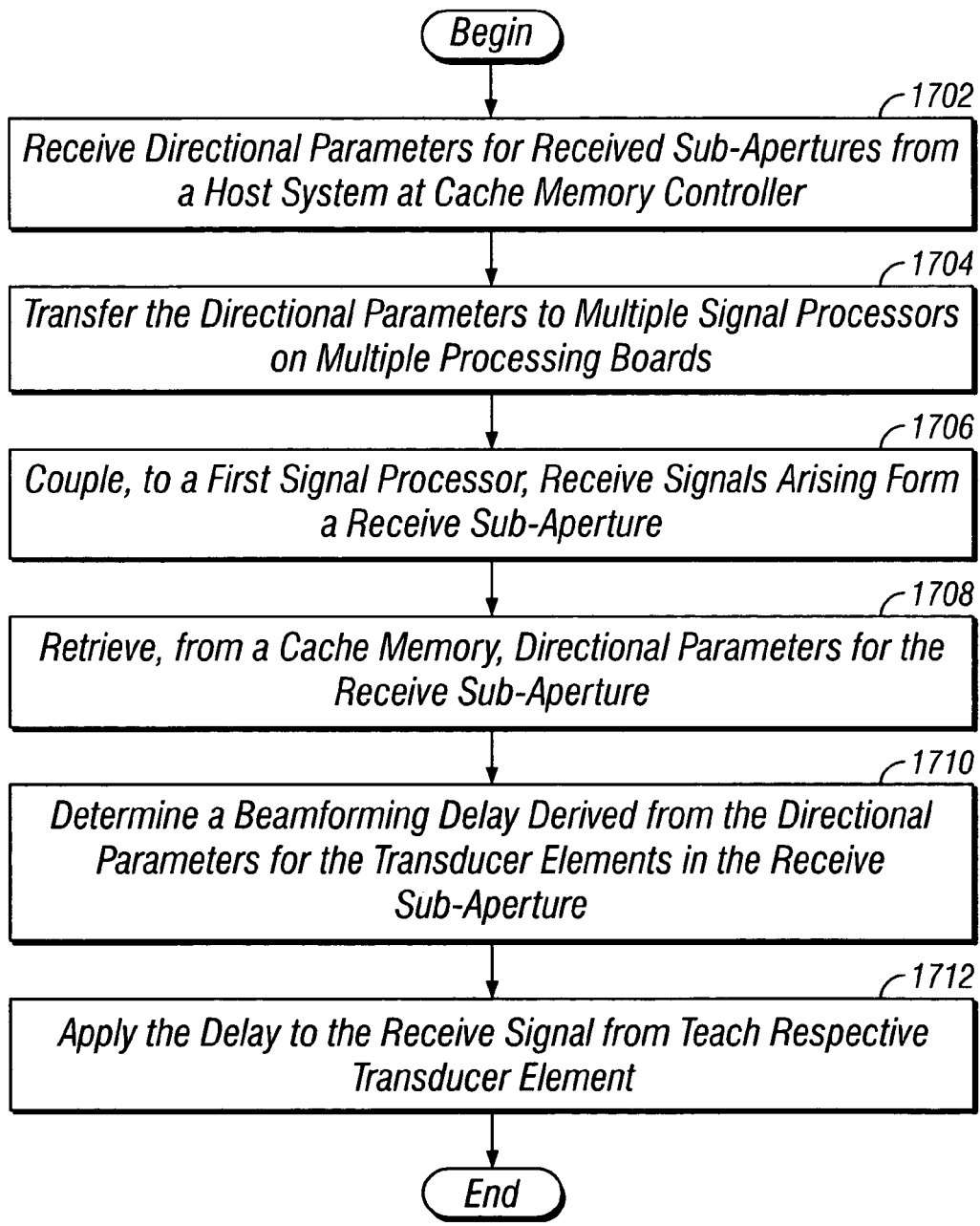
FIG. 17 illustrates steps that the ultrasound probe shown in FIG. 1 may take to perform beamforming in the probe.

FIG. 17 summarizes the steps 1700 that the ultrasound probe 100 shown in FIG. 1 may take to perform beamforming in the probe 100. The probe 100 receives multiple directional parameters such as inclination values (e.g., delta X and delta Y data) for the receive sub-apertures from a host system 116 at a cache memory and controller 112 (Step 1702). The cache memory and controller 112 then transfers the directional parameters to multiple signal processors 110 on multiple processing boards 106 (Step 1704).

The probe 100 couples to signal processors 110, receive signals arising from a receive sub-aperture (Step 1706). The signal processor 110 retrieves, from the serial input registers (e.g., 1302-1304, 1306-1308, 1310-1312, or 1314-1316), directional parameters for the receive sub-aperture (Step 1708). Based on the directional parameters, the signal processor determines a beamforming delay for the transducer elements in the receive sub-aperture (Step 1710), and applies the delay to the receive signal from each respective transducer element (Step 1712).

FIG. 18 shows steps 1800 that the ultrasound probe 100 shown in FIG. 1 (e.g., using the transceiver circuitry 700 may take to transmit and receive energy to an acoustic transducer element multiplexed between a receive aperture and a transmit aperture.) The circuitry 700 couples a transmit pulse through a transmit section input 704, a transmit section output 706, and receive signal blocking circuitry D1, D3 and Cshunt coupled between the transmit section input 704 and the transmit section output 706 (Step 1802). The transceiver circuitry 700 also couples a receive signal through a receive section input 712, a receive section output 710, and transmit signal blocking circuitry C2 and D4, and Ccouple and D2, coupled between the receive section input 712 and the receive section output 710 (Step 1804).

Figure 19:
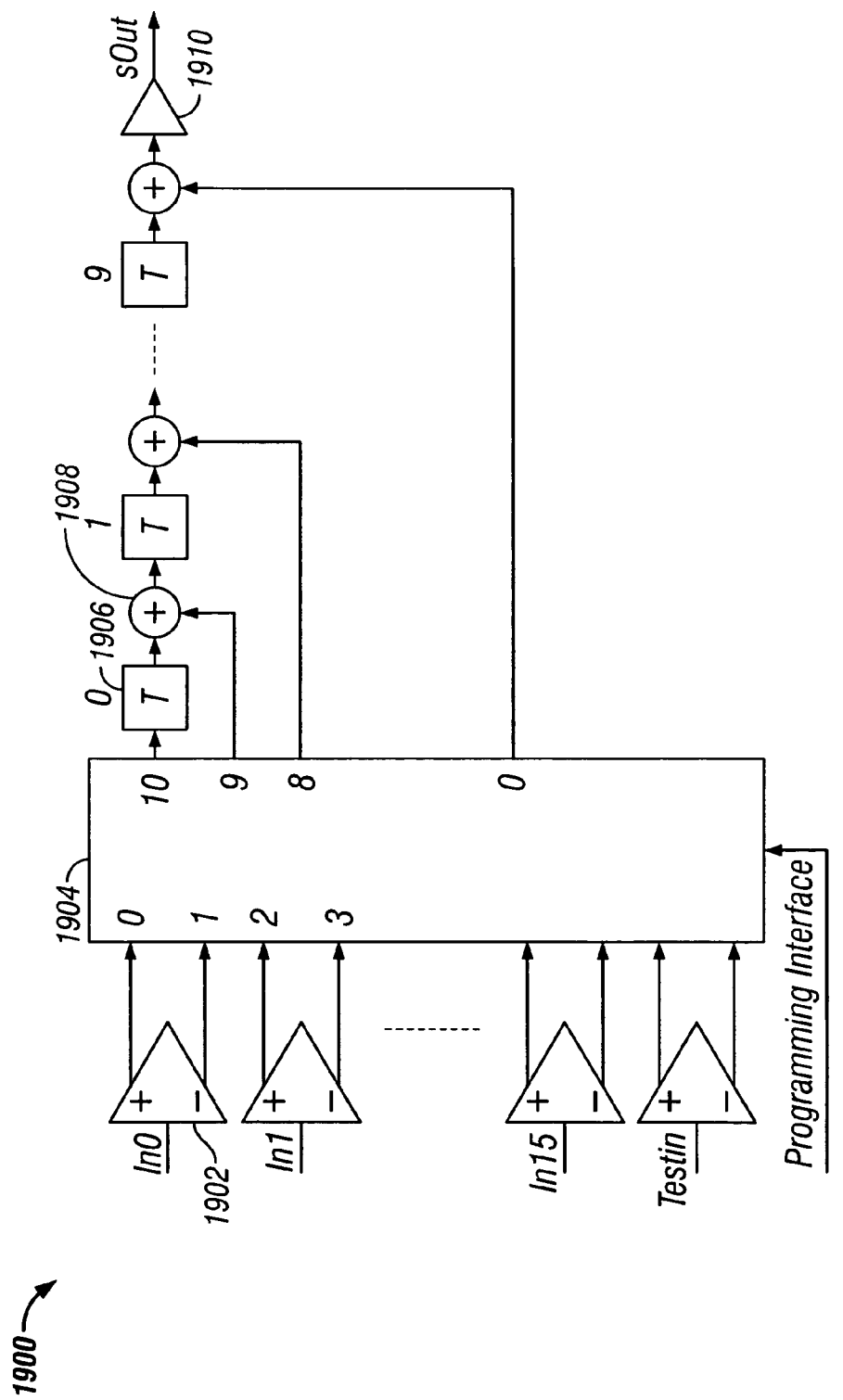
FIG. 19 shows another implementation of beamforming circuitry for the signal processors.

Turning next to FIG. 19, that figure shows a block diagram 1900 of another implementation of beamforming circuitry in the aperture processors 902-908. The beamforming circuitry 1900 includes the pre-amplifiers 1902, one for each of sixteen receive channels in a receive aperture, and one for testing. The pre-amplifiers 1902 are connected to a 34×11 cross-point matrix 1904 that flexibly connects the receive signals through zero to ten delay elements 1906 and summing nodes 1908 that form, in series, a delay line. The line driver 1910 drives the combined signal back to the host system 116.

The cross-point matrix 1904 supports the connection of any receive channel to any node of the delay line. When several channels are connected to the same node of the delay line, then the output of that node is the sum of the respective input signals. Any channel may be inverted before entering a summing node, and any channel may optionally be simultaneously connected to two adjacent summing nodes. In that case, the signal will then split so that the effective gain is reduced by approximately 6 dB for each.

When the beamforming circuitry 1900 is employed, the cross-point controller 1500 outputs the following signals to the beamforming circuitry 1900: intPol, chPos(4).

Figure 11:
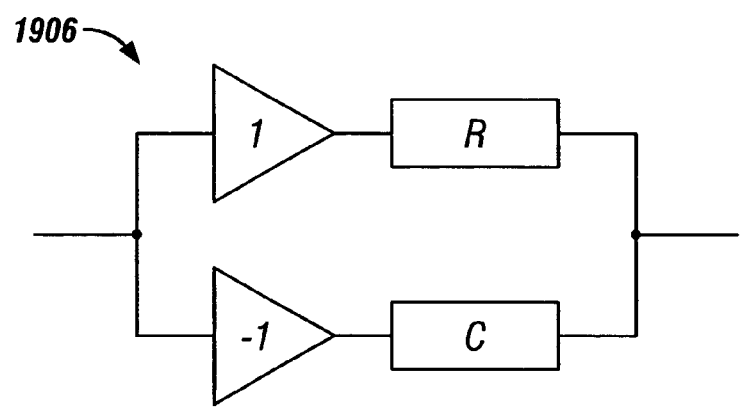
FIG. 11 shows an all-pass filter cell.

FIG. 11 shows one implementation for an all-pass filter cell (e.g., the filter cell 1906). As shown, the all-pass filters may be implemented as a non-inverting buffer followed by a resistor R, in parallel with an inverting buffer in series with a capacitor C. Each filter cell has a phase delay of T=2RC, and a transfer function of $Hc(w)=(1-j(wT/2))/(1+j(wT/2))$.

Figure 12:
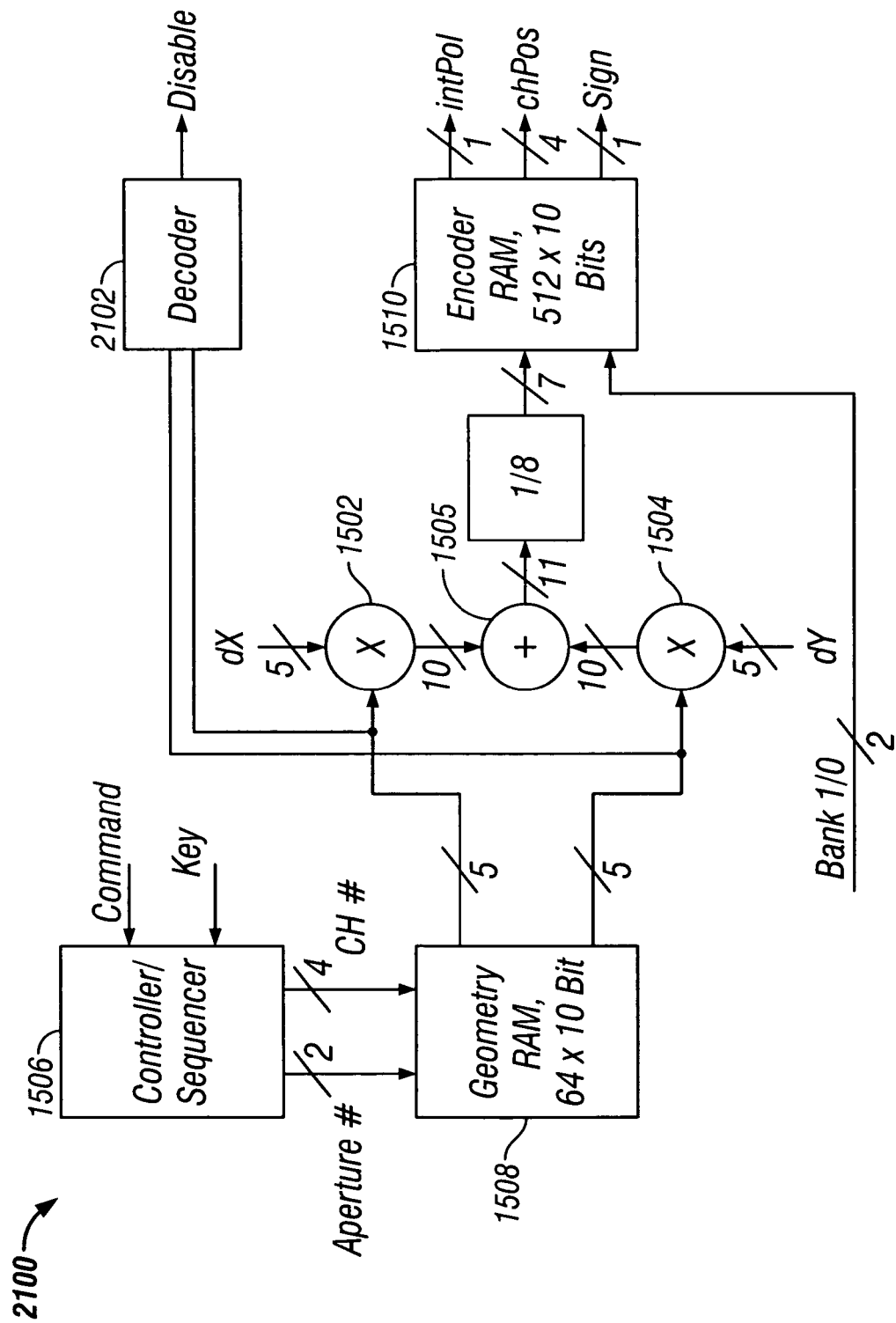
FIG. 12 shows a second implementation of a cross-point controller.

FIG. 12 shows a cross-point controller 2100 for use with the beamforming circuitry 1900 to program the switches in the cross-point matrix 1904, starting on a trigger event and operating on the latched version of the scan parameters. The cross-point controller 2100 sequences through all transducer element receive inputs 'n' for every receive aperture 'm' handled by the signal processor 110. The cross-point controller 2100 may be considered to determine a preliminary scaled version of the delay to be introduced to each receive signal as: floor((x(m,n)*deltaX(m)+y(m,n)*deltaY(m))/8), for n=0, 1, ... 15, and m=0, 1, 2, 3.

Note that x(m,n) and y(m,n) are the geometrical positions of the transducer element coupled to the nth input for receive aperture m. A reserved code may be established (e.g., x(m,n), y(m,n)=−16, −16) that disables (e.g., for power management) channel n of the aperture m by using the decoder 2102 to detect the code (or optionally or in addition, overflow of chPos), and assert a channel disable output signal. The positions are indexed through the geometry RAM 1508 to add routing flexibility during processing circuit board 106 layout. The scale factors deltaX(m) and deltaY(m) may remain constant for all receive signals in a given receive aperture m.

The preliminary delay is converted into a physical delay through a table look-up in the encoder RAM 1510. In one implementation, the output of the encoder RAM 1510 includes six bits: one bit for intPol, four bits for chPos, and one bit for sing. The chPos bits cause the corresponding switch in the cross-point matrix 1904 to be closed. If the control bit intPol is set, the switch 1+chPos will also be set. The sign bit selects the non-inverted or inverted version of the input signal.

While various embodiments of the invention have been described, it will be apparent to those of ordinary skill in the art that many more embodiments and implementations are possible that are within the scope of this invention.

What is claimed is:

1. A sub-aperture transceiver system to be housed in an ultrasound probe, the system comprising:
a probe housing;
a signal processor located in the probe housing;
receive signal connections coupling the signal processor to
a receive sub-aperture comprising acoustic transceiver elements;

transmit signal connections coupled to a transmit sub-aperture comprising at least one acoustic transceiver element joined to multiplexing circuitry to multiplex the acoustic transceiver element between the transmit and receive sub-apertures, the signal processor performing beamforming on the receive sub-aperture to produce a receive sub-aperture signal; and a receive sub-aperture output driven by the signal processor for carrying the receive sub-aperture signal from the probe housing.

2. The system of claim 1, where the receive sub-aperture is a triangular sub-aperture.

3. The system of claim 1, where the transmit sub-aperture is square.

4. The system of claim 1, where the receive sub-aperture comprises at least two uneven rows of acoustic transceiver elements.

5. The system of claim 1, where the receive signal connections couple the signal processor to a plurality of receive sub-apertures.

6. The system of claim 1, where the transmit signal connections couple the signal processor to a plurality of transmit sub-apertures.

7. The system of claim 6, where the receive sub-apertures are triangular receive sub-apertures.

8. The system of claim 1, further comprising a plurality of signal processors coupled to a corresponding plurality of receive sub-apertures, each of the signal processors performing beamforming for the corresponding receive sub-aperture.

9. The system of claim 8, where the receive signal connections further couple each signal processor to the corresponding receive sub-apertures, the receive sub-apertures collectively forming a receive aperture.

10. The system of claim 1, wherein the multiplexing circuitry includes a receive signal blocking circuit coupled to the transmit signal connections to block the receive sub-aperture signal.

11. The system of claim 1, wherein the multiplexing circuitry includes a transmit signal blocking circuit connected to the receive signal connections to block transmit signals.

12. The system of claim 1, wherein the multiplexing circuitry includes a diode arrangement coupled to the transmit signal connections to block the receive sub-aperture signal.

13. The system of claim 1, wherein the multiplexing circuitry includes a diode arrangement connected to the receive signal connections to block transmit signals.

14. A sub-aperture transceiver system comprising:
a first processing board having a data input to receive first setup data;
a second processing board joined serially in a chained arrangement with the first processing board the second processing board having a data input to receive second setup data; and
receive signal connections for a plurality of receive sub-apertures distributed between the first and second processing boards, the first and second processing boards producing first and second receive data, respectively, based upon first and second setup data, the first and second setup data being propagated serially between the first processing board and the second processing board;
where the receive signal connections couple each receive sub-aperture to at least one of the first and second processing boards without partitioning any receive sub-aperture between the first and second processing boards.

15. The system of claim 14, further comprising:
transmit signal connections for a plurality of transmit sub-apertures distributed between the first and second processing boards,
where the transmit signal connections couple each transmit sub-aperture to at least one of the processing boards without partitioning any transmit sub-aperture between the processing boards.

16. The system of claim 14, further comprising:
transmit signal connections for a plurality of transmit sub-apertures distributed between the first and second processing boards,
where at least one transmit sub-aperture comprises a transducer element multiplexed between at least one receive sub-aperture.

17. The system of claim 16, where the transmit sub-apertures are square transmit sub-apertures.

18. The system of claim 14, further comprising a first cable bearing selected ones of the receive signal connections to the first processing board and a second cable bearing selected ones of the receive signal connections to the second processing board.

19. The system of claim 18, where the first and second cables are flex cables.

20. The system of claim 18, where the first cable comprises selected ones of the receive signal connections for a first transducer array line.

21. The system of claim 14, further comprising a first signal processor on the first processing board and a second signal processor on the second processing board.

22. The system of claim 21, where the first signal processor is coupled to a first plurality of receive sub-apertures through the receive signal connections and where the second signal processor is coupled to a second plurality of receive sub-apertures through the receive signal connections.

23. The system of claim 14, where the receive sub-apertures are triangular receive sub-apertures.

24. The system of claim 14, where the first and second processing boards are disposed in an ultrasound probe.

25. The system of claim 14, further comprising a controller connected over digital signal lines to the first and second processing boards, the controller passing at least one of static and dynamic setup information as the first and second setup data to the first and second processing boards.

26. The system of claim 14, wherein the first and second setup data include dynamic setup information that varies from receive beam to receive beam.

27. The system of claim 14, further comprising memory storing the first and second setup data organized into pages, where each page stores beam directional setup information associated with a complete scan sequence.

28. A method in an ultrasound system for sub-aperture processing, the method comprising:
performing sub-aperture beamforming, at a signal processor located in an ultrasound probe, based on a plurality of receive signals received from acoustic transducer elements that form a receive sub-aperture;
multiplexing, within the ultrasound probe, at least one of the acoustic transducer elements between the receive sub-aperture and a transmit sub-aperture; and
driving a receive sub-aperture output by the signal processor with a receive sub-aperture signal obtained over the acoustic transducer elements in the receive sub-aperture.

29. The method of claim 28, where the receive sub-aperture is a triangular sub-aperture.

30. The method of claim 28, where the transmit sub-aperture is square.

31. A method in an ultrasound system for sub-aperture processing, the method comprising:
- receiving, for a plurality of receive sub-apertures, receive signals distributed to a first signal processor on a first processing board and a second signal processor on a second processing board without partitioning any of the receive sub-apertures between the processing boards;
- multiplexing, within the ultrasound probe, at least one of the acoustic transducer elements between a receive sub-aperture and a transmit sub-aperture; and
- driving a receive sub-aperture output by the first signal processor with a receive sub-aperture signal obtained over the acoustic transducer elements in the receive sub-aperture.

32. A method in an ultrasound system for sub-aperture processing, the method comprising:
- receiving, at a signal processor located in an ultrasound probe, a plurality of receive signals from acoustic transducer elements that comprise a receive sub-aperture;
- multiplexing, within the ultrasound probe, at least one of the acoustic transducer elements between the receive subaperture and a transmit sub-aperture;
- driving a receive sub-aperture output coupled to the signal processor with a signal obtained over the acoustic transducer elements in the receive sub-aperture;
- coupling transmit signals to a plurality of transmit apertures over transmit signal connections distributed between the first and second processing boards, and
- where the transmit signal connections couple each transmit sub-aperture to at least one of the processing boards without partitioning any of the transmit sub-apertures between the processing boards.

* * * * *